(12) United States Patent
Doxsey et al.

(10) Patent No.: US 9,409,978 B2
(45) Date of Patent: Aug. 9, 2016

(54) MODULATION OF MIDBODY DERIVATIVES

(75) Inventors: Stephen J. Doxsey, Sterling, MA (US);
Tse-Chun Kuo, Worcester, MA (US);
Chun-Ting Chen, Worcester, MA (US)

(73) Assignee: University of Massachusetts, Boston, MA (US)

( * ) Notice: Subject to any disclaimer, the term of this patent is extended or adjusted under 35 U.S.C. 154(b) by 29 days.

(21) Appl. No.: 14/342,662

(22) PCT Filed: Sep. 7, 2012

(86) PCT No.: PCT/US2012/054282
§ 371 (c)(1),
(2), (4) Date: Apr. 22, 2014

(87) PCT Pub. No.: WO2013/036850
PCT Pub. Date: Mar. 14, 2013

(65) Prior Publication Data
US 2014/0314836 A1    Oct. 23, 2014

Related U.S. Application Data

(60) Provisional application No. 61/533,036, filed on Sep. 9, 2011.

(51) Int. Cl.
*C12N 15/86* (2006.01)
*A61K 38/00* (2006.01)
*C07K 16/18* (2006.01)
*C07K 14/47* (2006.01)

(52) U.S. Cl.
CPC .............. *C07K 16/18* (2013.01); *C07K 14/47* (2013.01); *C07K 2317/31* (2013.01)

(58) Field of Classification Search
CPC ............................. C12N 15/86; A61K 38/00
USPC ..................... 424/93.6, 93.1, 277.1
See application file for complete search history.

(56) References Cited

U.S. PATENT DOCUMENTS

| 7,682,799 | B2 | 3/2010 | Doxsey et al. | |
| 2004/0126824 | A1* | 7/2004 | Liu | C07K 14/47 435/7.23 |
| 2005/0176669 | A1* | 8/2005 | Al-Murrani | C12N 15/113 514/44 A |

FOREIGN PATENT DOCUMENTS

WO    WO 2008/079269    7/2008

OTHER PUBLICATIONS

Ovarian Cancer-Adenocarcinoma of the Ovary Oct. 10, 2015.*
Anderson et al., "Centriole Age Underlies Asynchronous Primary Cilium Growth in Mammalian Cells", Curr Biol., vol. 19:1498-1502 (2009).
Bjorkoy et al., "p62/SQSTM1 forms protein aggregates degraded by autophagy and has a protective effect on huntingtin-induced cell death", JCB, vol. 171:603-614 (2005).
Cecconi et al., "The Role of Autophagy in Mammalian Development: Cell Makeover Rather than Cell Death", Dev Cell, vol. 15:344-357 (2008).
Goss et al., "Both daughter cells traffic and exocytose membrane at the cleavage furrow during mammalian cytokinesis", The Journal of Cell Biology, vol. 181:1047-1054 (2008).
Kirkin et al., "A role for NBR1 in autophagosomal degradation of ubiquitinated substrates", Molecular Cell, vol. 33:505-516 (2009).
Klionsky et al., "Guidelines for the use and interpretation of assays for monitoring autophagy in higher eukaryotes", Autophagy, vol. 4:151-175 (2008).
Kuo et al., "Midbody accumulation through evasion of autophagy contributes to cellular reprogramming and tumorigenicity", Nature Cell Biology, vol. 13:1214-1223 (2011).
Levine et al., "Autophagy in the Pathogenesis of Disease", Cell, vol. 132:27-42 (2008).
Mullins et al., "Terminal Phase of Cytokinesis in D-98S Cells", The Journal of Cell Biology, vol. 73:672-684 (1977).
Pankiv et al., "p62/SQSTM1 Binds Directly to Atg8/LC3 to Facilitate Degradation of Ubiquitinated Protein Aggregates by Autophagy", The Journal of Biological Chemistry, vol. 282:24131-14145 (2007).
Piel et al., "The Respective Contributions of the Mother and Daughter Centrioles to Centrosome Activity and Behavior in Vertebrate Cells", The Journal of Cell Biology, vol. 149:317-329 (2000).
Pohl et al., "Midbody ring disposal by autophagy is a post-abscission event of cytokinesis", Nat. Cell Biol., vol. 11:65-70 (2008).
Salic et al., "A chemical method for fast and sensitive detection of DNA synthesis in vivo", PNAS, vol. 105:2415-2420 (2008).
Sarkar et al., "A rational mechanism for combination treatment of Huntington's disease using lithium and rapamycin,", Human Molecular Genetics, vol. 17:170-178 (2008).
Wang et al., "Asymmetric centrosome inheritance maintains neural progenitors in neocortex", Nature, vol. 461:947-955 (2009).
Yamashita et al., "Asymmetric inheritance of mother versus daughter centrosome in stem cell division", Science, vol. 315:518-521 (2007).
Notification Concerning Transmittal of International Preliminary Report on Patentability (Chapter I of the Patent Cooperation Treaty), Int. Appl. No. PCT/US2012/054282, mailed on Mar. 20, 2014 (9 pages).
Notification of Transmittal of the International Search Report and the Written Opinion of the International Searching Authority, or the Declaration, Int. Appl. No. PCT/US2012/054282, dated Mar. 4, 2013 (14 pages).

* cited by examiner

*Primary Examiner* — Yan Xiao
(74) *Attorney, Agent, or Firm* — Fish & Richardson P.C.

(57) ABSTRACT

The number of midbody derivatives in a cell may be modulated by modulating autophagy induced by NBR1. Exemplary methods include modulating the amount or activity of NBR1 in the cell, potentiating or inhibiting binding between NBR1 and Cep55 in the cell, or modulating the amount of Cep55 in the cell. These methods can be used in the treatment of cancers or in methods of reprogramming cells.

20 Claims, 11 Drawing Sheets

MODULATION OF MIDBODY DERIVATIVES

CROSS-REFERENCE TO RELATED APPLICATIONS

This application is a national phase application under 35 U.S.C. §371 of PCT International Application No. PCT/US2012/054282, filed Sep. 7, 2012, which claims the benefit under 35 USC §119(e) of U.S. Provisional Patent Application Ser. No. 61/533,036, filed on Sep. 9, 2011, the entire contents of these applications are hereby incorporated by reference.

STATEMENT OF FEDERALLY SPONSORED RESEARCH

This invention was made with Government support under grant number GM051994 awarded by the National Institutes of Health. The Government has certain rights in the invention.

BACKGROUND

Breast cancer is a multi-stage disease that initially develops from epithelial lesions confined to breast ducts and lobules (carcinoma in-situ), which then rapidly progresses to become locally invasive and finally metastatic. Despite being the most common cancer of women and the second leading cause of cancer mortality among women, the underlying cause(s) of breast cancer remain(s) unknown. If discovered in its earliest stages, breast cancer can be treated successfully. However, if the initial tumor goes undetected prognosis is poor and more radical treatments are initiated including mastectomy, radiation, and chemotherapy, none of which is able to cure malignant breast carcinoma. Therefore, new insights into breast tumor biology and the underlying etiology of the disease may serve as an inroad to effective drug treatments.

The midbody (MB) is a singular organelle formed between daughter cells during cytokinesis and required for their final separation. Remnants of MBs can persist in cells long after division as midbody derivatives (MBds), but their fate is unclear.

SUMMARY

This disclosure is based, in part, on the surprising discovery that MBds are inherited asymmetrically by the daughter cell with the older centrosome. MBds were found to selectively accumulate in stem cells, induced pluripotent stem cells (iPSCs) and potential cancer 'stem cells' (CSCs) in vivo and in vitro. MBd loss accompanied stem cell differentiation, and involved autophagic degradation mediated by binding of the autophagic receptor, Neighbor of BRCA 1 (NBR1), to the MB protein, Centrosomal Protein of 55 kDa (Cep55). Differentiating cells and normal dividing cells did not accumulate MBds and were observed to possess high autophagic activity. Stem cells and cancer cells accumulated MBds by evading autophagosome encapsulation and exhibited low autophagic activity. MBd enrichment was shown to enhance reprogramming to iPSCs and increase in vitro tumorigenicity of cancer cells.

Accordingly, this disclosure features, in one aspect, methods of inducing degradation of a midbody derivative in a cell (e.g., a cancer cell or cancer stem cell) that include (a) increasing the amount of NBR1 in the cell; or (b) potentiating binding between NBR1 and Cep55 in the cell, thereby inducing degradation of a midbody derivative in the cell. In some embodiments, the cell can be in a subject.

In some embodiments, increasing the amount of NBR1 in the cell includes introducing into the cell a nucleic acid that expresses NBR1, or a fragment or variant thereof. The nucleic acid can be in a vector, e.g., a viral vector (e.g., an adenovirus vector, an adeno-associated virus vector, a retrovirus vector, or a lentivirus vector).

In some embodiments, increasing the amount of NBR1 in the cell includes introducing into the cell a composition that includes an NBR1 polypeptide, or a fragment or variant thereof, or an artificial transcription factor that increases transcription of the NBR1 gene. The composition can include the NBR1 polypeptide (or fragment or variant thereof) or artificial transcription factor fused with a cell-penetrating peptide (e.g., an internalization peptide sequence of internalization peptide sequence of a protein selected from the group consisting of: Tat, Antennapedia, VP22, Pep-1, and transportan). The composition can include a liposome.

In some embodiments, potentiating binding between NBR1 and Cep55 in the cell includes introducing into the cell an agent that binds both NBR1 and Cep55, e.g., a polypeptide or antibody that binds to both NBR1 and Cep55.

In another aspect, the disclosure features methods of treating cancer (e.g., breast cancer) in a subject (e.g., a human) that include: (a) increasing the amount of NBR1 in a cancer cell or cancer stem cell in the subject; or (b) potentiating binding between NBR1 and Cep55 in a cancer cell or cancer stem cell in the subject, thereby treating cancer in the subject. The disclosure also features the use of (a) an agent that increases the amount of NBR1 in a cancer cell or cancer stem cell; or (b) an agent that potentiates binding between NBR1 and Cep55 in a cancer cell or cancer stem cell for treatment of a cancer (e.g., a breast cancer) in a subject (e.g., a human) or in the preparation of a medicament for treatment of a cancer (e.g., breast cancer) in a subject (e.g., a human). The disclosure also features agents that increase the amount of NBR1 in a cancer cell or cancer stem cell or that potentiate binding between NBR1 and Cep55 in a cancer cell or cancer stem cell for use in treatment of a cancer (e.g., a breast cancer) in a subject (e.g., a human).

In some embodiments, increasing the amount of NBR1 in the cell includes introducing into the cell a nucleic acid that expresses NBR1, or a fragment or variant thereof. The nucleic acid can be in a vector, e.g., a viral vector (e.g., an adenovirus vector, an adeno-associated virus vector, a retrovirus vector, or a lentivirus vector).

In some embodiments, increasing the amount of NBR1 in the cell includes introducing into the cell a composition that includes an NBR1 polypeptide, or a fragment or variant thereof, or an artificial transcription factor that increases transcription of the NBR1 gene. The composition can include the NBR1 polypeptide (or fragment or variant thereof) or artificial transcription factor fused with a cell-penetrating peptide (e.g., an internalization peptide sequence of internalization peptide sequence of a protein selected from the group consisting of: Tat, Antennapedia, VP22, Pep-1, and transportan). The composition can include a liposome. The composition can be administered systemically or locally to the vicinity of the cancer cell or cancer stem cell.

In one aspect, the disclosure features bispecific antibodies or fragments thereof that bind to both NBR1 and Cep55. The antibodies can function to increase degradation of a midbody derivative in a cell (e.g., a cancer cell or cancer stem cell).

In another aspect, the disclosure features methods of inhibiting degradation of a midbody derivative in a cell that include (a) decreasing the amount of NBR1 in the cell; (b) increasing the amount of Cep55 in the cell; or (c) inhibiting binding between NBR1 and Cep55 in the cell, thereby inhibiting degradation of a midbody derivative in the cell.

In some embodiments, decreasing the amount of NBR1 in the cell includes introducing into the cell a nucleic acid that inhibits NBR1 expression (e.g., an siRNA, shRNA, microRNA, ribozyme, or antisense polynucleotide).

In some embodiments, decreasing the amount of NBR1 in the cell includes introducing into the cell a composition that includes an artificial transcription factor that decreases transcription of the NBR1 gene. The artificial transcription factor can be fused with a cell-penetrating peptide (e.g., an internalization peptide sequence of internalization peptide sequence of a protein selected from the group consisting of: Tat, Antennapedia, VP22, Pep-1, and transportan). The composition can include a liposome.

In some embodiments, inhibiting binding between NBR1 and Cep55 in the cell includes introducing into the cell an agent (e.g., an antibody or fragment thereof) that binds NBR1 or Cep55 and inhibits binding between NBR1 and Cep55.

In one aspect, the disclosure features methods of aiding reprogramming of a cell or maintaining a cell in a dedifferentiated state that include (a) decreasing the amount of NBR1 in the cell; (b) increasing the amount of Cep55 in the cell; or (c) inhibiting binding between NBR1 and Cep55 in the cell, thereby aiding reprogramming of the cell.

In some embodiments, decreasing the amount of NBR1 in the cell includes introducing into the cell a nucleic acid that inhibits NBR1 expression (e.g., an siRNA, shRNA, microRNA, ribozyme, or antisense polynucleotide).

In some embodiments, decreasing the amount of NBR1 in the cell includes introducing into the cell a composition that includes an artificial transcription factor that decreases transcription of the NBR1 gene. The artificial transcription factor can be fused with a cell-penetrating peptide (e.g., an internalization peptide sequence of internalization peptide sequence of a protein selected from the group consisting of: Tat, Antennapedia, VP22, Pep-1, and transportan). The composition can include a liposome.

In some embodiments, inhibiting binding between NBR1 and Cep55 in the cell includes introducing into the cell an agent (e.g., an antibody or fragment thereof) that binds NBR1 or Cep55 and inhibits binding between NBR1 and Cep55.

"Polypeptide" and "protein" are used interchangeably and mean any peptide-linked chain of amino acids, regardless of length or post-translational modification.

The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This disclosure provides new roles for MBds outside of cytokinesis. Disclosed herein is evidence of MBd-accumulation in stem cells, hESCs and iPSCs in vivo and in vitro, and dramatic MBd reduction in differentiating progeny of stem cells. Evidence is presented that MBds function in maintaining or enhancing the pluripotency of stem cells and the tumorigenicity of cancer cells.

Figure 7:
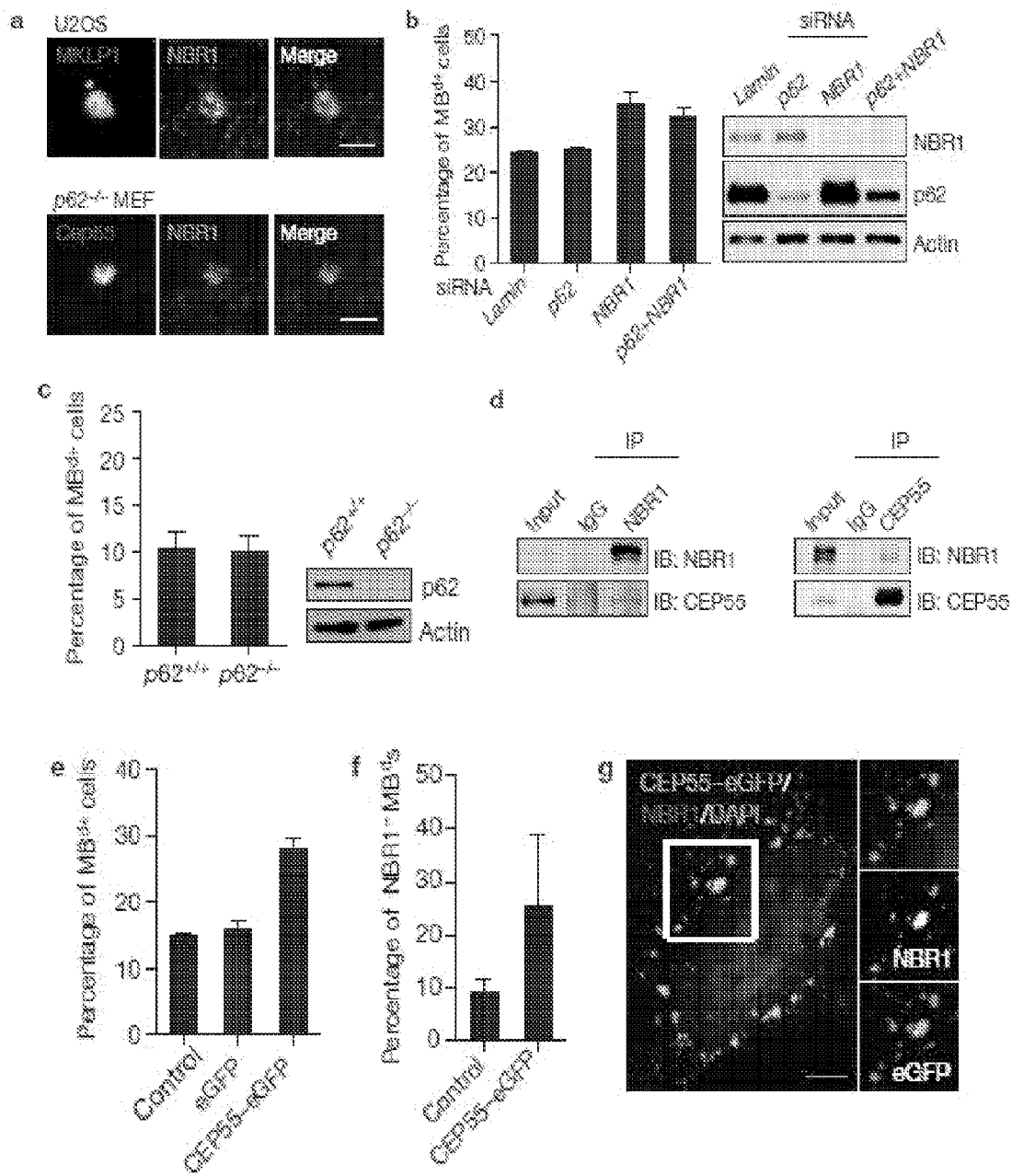
FIG. 7. NBR1 is a receptor for targeting MBds to the autophagy pathway. (a) Single-plane confocal images showing co-localization of the MBd and the autophagic receptor, NBR1, in U2OS cells and p62-deleted MEFs. MBd markers: MKLP1 or Cep55. Bar, 2 μm. (b) The percent of MBd+ cells is significantly increased following the depletion of NBR1 (p=0.022, n=3), but not another autophagic receptor, p62. Co-depletion of NBR1 and p62 does not further increase MBd levels over NBR1 depletion alone. (c) Deletion of the p62 gene does not affect the percent of MBd+ cells. For (b) and (c), immunoblots verify protein loss. (d) Co-immunoprecipitation reveals Cep55 and NBR1 form a complex. Precipitated proteins and 5% of the input material (Input) were analyzed by immunoblotting with antibodies against NBR1 or Cep55. (e-g) Over-expression of CEP55-EGFP increases the percent of MBd+ cells (e; p=0.0007, n=3) and the percent of NBR1-negative MBds (f; p=0.0568, n=3), presumably by sequestering NBR1 (red) away from MBds in cells expressing CEP55-EGFP (green) as shown in (g), and consequently preventing MBd degradation. The dotted box in (g) is enlarged (top right panel), and the labeling of NBR1 and CEP55-EGFP (middle and bottom right panel) are also presented. DAPI, DNA (blue). Bar, 5 µm. The data are presented as mean±s.d. (b, c, e, and f).
Figure 8:
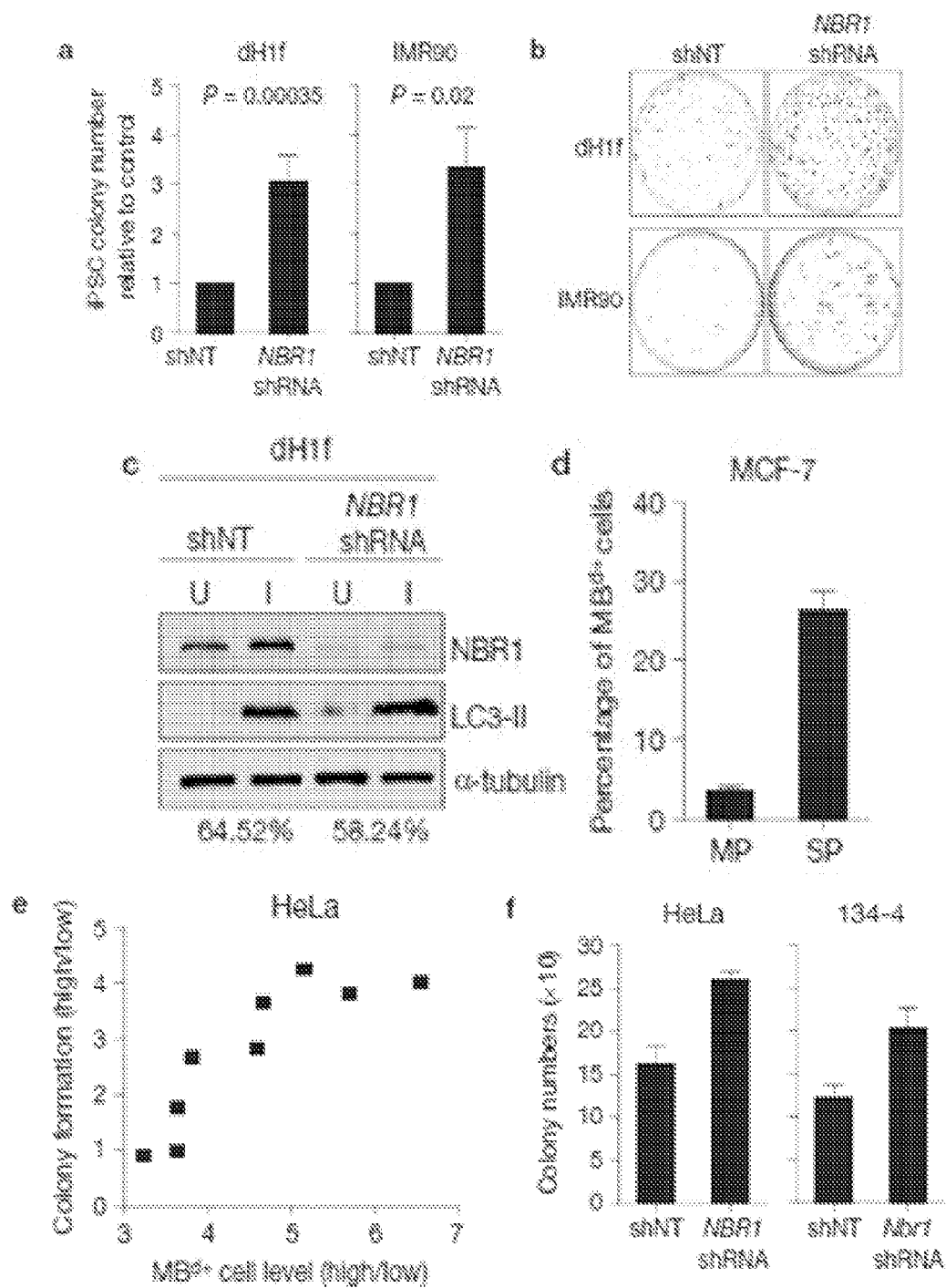
FIG. 8. MBd enrichment increases reprogramming efficiency and enhances in vitro tumorigenicity. (a-c) Reprogramming is more efficient after MBd enrichment. Differentiated cells (dH1f) and embryonic fibroblasts (IMR90) are reprogrammed after stable expression of either NBR1-specific shRNA (shNBR1) or non-targeting shRNA (shNT). Emerging iPSC colonies are scored based on Tra-1-60 expression37. (a, b) Cells depleted of NBR1 to increase MBd levels show an increase in iPSC colony formation (a, dH1f: 3.1±0.5-fold, n=15, p=0.00035; IMR90: 3.4±0.8-fold, n=3, p=0.02; data are mean±s.e.m.) but insignificant changes in autophagic activity (c) over shNT control. (b) Representative plates with Tra-1-60-immunostained iPSC colonies. Immunoblot (c, top) and densitometry (c, bottom; percent of autophagic flux) show representative result (n=3); α-tubulin, loading control. (d) MCF-7 side-population (SP) cells have a significantly higher percentage of MBd+ cells over the non-SP population (MP; p=0.0015, n=3; data are mean±s.d.). (e, f) MBd enrichment in cancer cells leads to increased anchorage-independent growth. MKLP1-GFP-expressing HeLa cells are separated into "MBd high" and "MBd low" subpopulations. An increase in the "MBd high" over "MBd low" ratio is associated with an increase in soft-agar colony formation (e). No significant difference was observed when the enrichment of MBd high subpopulation was less than 3-fold. More soft-agar colonies are formed when MBds are enriched by NBR1-depletion (shNBR1) in HeLa (f, left; p=0.0012, n=3) and mouse 134-4 cells (f, right; p=0.0086, n=3); control, shNT. Data are mean±s.d., and the colony number (e, f) is the sum of INT-violet-stained colonies from 10 random fields. (g) Model for MBd fate in cells. The newly-formed MBd is preferentially inherited by the daughter cell with the older centrosome (top panel). The inherited MBd (black ring) is recognized by binding of the NBR1 autophagic receptor (grey circle) with the MB protein Cep55 (magenta). The MBd is then encapsulated by the autophagosome (yellow circle), and degraded after fusion of autophagosome and lysosome (red circle) in differentiated cells. This pathway prevents MBd-accumulation. In contrast, stem cells efficiently accumulate MBds through successive divisions and evasion of NBR1-mediated autophagy. Additionally, differentiated and stem cells possess overall high and low autophagic activity, respectively.
Figure 8:
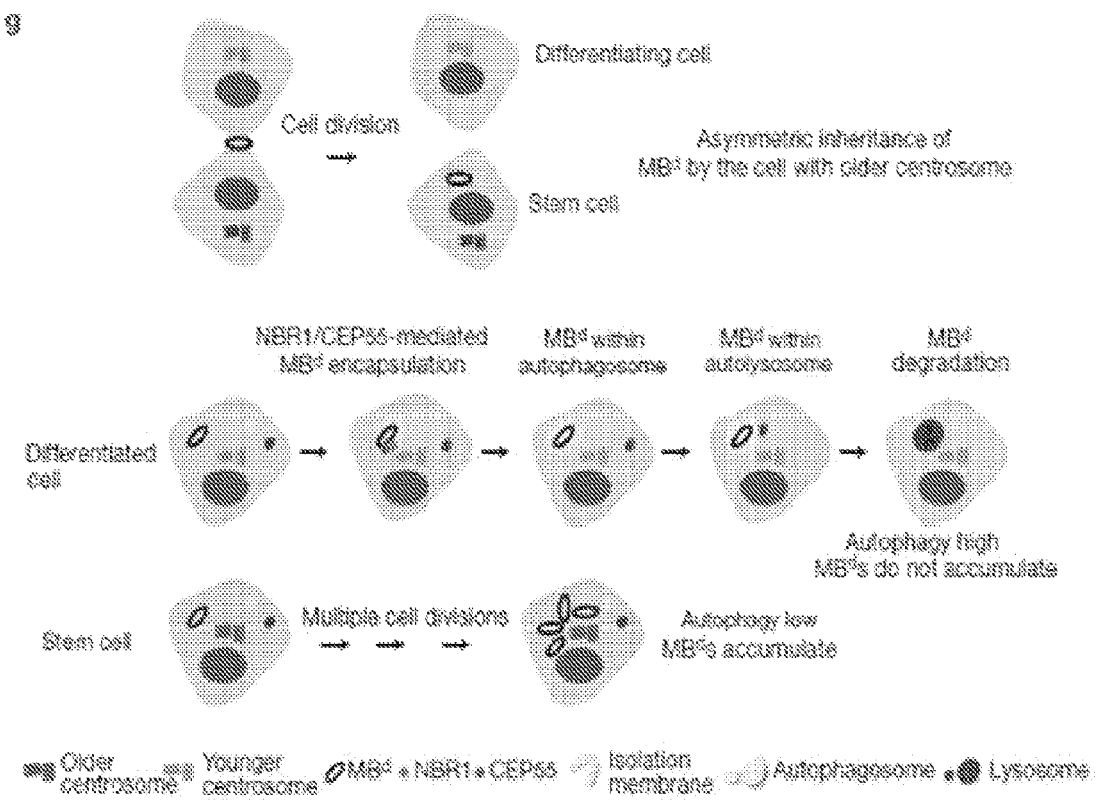

The findings disclosed herein indicate that MBd loss that accompanies stem cell differentiation is mediated by autophagic degradation, resulting in selective elimination of MBds in differentiated cells but retention in germ or stem cells. Additionally, essentially all cancer cells examined contained MBd-accumulating subpopulations, making this a common intrinsic property of both stem cells and cancer cells. The observation that MBd-enriched cancer subpopulations exhibited enhanced in vitro tumorigenicity is consistent with the CSC model for potentiation of tumorigenicity. Evasion of autophagic degradation is disclosed as a mechanism for MBd-accumulation (FIG. 8g, bottom). This is exemplified by the inverse relationship between MBd levels and autophagic activity, and by changes in MBd levels with manipulation of autophagy levels. MBd-accumulation can also be mediated by uncoupling receptor-mediated entry into the autophagy pathway, since depletion of the NBR1 autophagic receptor or over-expression of the corresponding ligand, Cep55, increases MBd levels. In contrast, another known autophagic receptor, p62, does not appear to be involved in MBd clearance (FIG. 7b, c). Since NBR1-silencing increases MBds to levels seen following inhibition of autophagy in HeLa cells (FIGS. 6b and 7b), NBR1-mediated autophagic degradation can represent a pathway for selective MBd elimination. The results presented herein indicate that Cep55 and NBR1 act as switches that control MBd fate.

Midbody Derivatives

Midbody derivatives (MBds) are structures related to the midbody. MBds can persist through several subsequent cell divisions, such that multiple MBds can be detected in some cells. MBDs are described in detail in U.S. Pat. No. 7,682,799.

The MBd structure is localized adjacent to the plasma membrane, and is made up of several proteins, including those listed in Table 1. The MBd contains many of the proteins present in the midbody, with some exceptions; for example, in some embodiments, γ-tubulin, which is a component of the midbody, is not present in MBds. The polypeptide components of MBds include kinases, other regulatory proteins, and structural proteins.

TABLE 1

Exemplary Polypeptide Components of Mammalian Midbody Derivatives

| Protein name | EntrezGene database ID | Also known as |
| --- | --- | --- |
| mitotic kinesin-like protein 1 (MKLP1) | GeneID: 9493 | KIF-23; CHO1; KNSL5; and MKLP-1 |
| Epsilon tubulin (ε-tubulin) | GeneID: 51175 | TUBE1, TUBE; FLJ22589; and dJ142L7.2 |
| Centrosomal Protein 55 kDa (Cep55) | GeneID: 55165 | URCC6; C10orf3; and FLJ10540 |
| Aurora B kinase | GeneID: 9212 | AIK2; AIM1; ARK2; AurB; IPL1; STK5; AIM-1; and STK12 |

The results described herein implicate Cep55 in autophagy of MBds. An exemplary human Cep55 protein sequence (GenBank NP_060601.3) is SEQ ID NO: 1.

Exemplary regions and sites of the Cep55 polypeptide sequence of SEQ ID NO: 1 are as follows:

```
Region      <118..>396
            /region_name="SMC_prok_B"
            /note="chromosome segregation protein SMC, common
            bacterial type; TIGR02168"
            /db_xref="CDD:162739"
Region      157..236
            /region_name="Interaction with TSG101"
            /experiment="experimental evidence, no additional details
            recorded"
            /note="propagated from UniProtKB/Swiss-Prot (Q53EZ4.3)"
Region      160..214
            /region_name="Interaction with PDCD6IP"
            /experiment="experimental evidence, no additional details
            recorded"
            /note="propagated from UniProtKB/Swiss-Prot (Q53EZ4.3)"
```

-continued

```
Region     171..205
           /region_name="EABR"
           /note="TSG101 and ALIX binding domain of CEP55;
           pfam12180"
           /db_xref="CDD:152615"
Region     355..464
           /region_name="Required for localization to the interphase
           centrosome and to the midbody during cytokinesis"
           /experiment="experimental evidence, no additional details
           recorded"
           /note="propagated from UniProtKB/Swiss-Prot (Q53EZ4.3)"
Site       425
           /site_type="phosphorylation"
           /experiment="experimental evidence, no additional details
           recorded"
           /note="Phosphoserine, by CDK1 and MAPK1; propagated from
           UniProtKB/Swiss-Prot (Q53EZ4.3)"
Site       428
           /site_type="phosphorylation"
           /experiment="experimental evidence, no additional details
           recorded"
           /note="Phosphoserine, by CDK1 and MAPK1; propagated from
           UniProtKB/Swiss-Prot (Q53EZ4.3)"
Site       430
           /site_type="phosphorylation"
           /experiment="experimental evidence, no additional details
           recorded"
           /note="Phosphothreonine; propagated from
           UniProtKB/Swiss-Prot (Q53EZ4.3)"
Site       436
           /site_type="phosphorylation"
           /experiment="experimental evidence, no additional details
           recorded"
           /note="Phosphoserine, by PLK1; propagated from
           UniProtKB/Swiss-Prot (Q53EZ4.3)"
```

An exemplary Cep55 nucleic acid sequence (GenBank NM_018131.4) is SEQ ID NO: 2.

Autophagy

During autophagy, double membrane-bound autophagosomes assemble, engulf cytoplasmic material, and fuse with lysosomes for degradation (Mizushima et al., 2008, Nature, 451:1069-75; Mizushima et al., 2007, Annu Rev. Nutr., 27:19-40; Yorimitus et al., 2007, Trends Cell Biol., 17:279-285; Levine et al., 2008, Cell, 132:27-42). Autophagy is required for cellular homeostasis, eliminating defective ubiquitin-tagged proteins and organelles (Mizushima et al., 2007, Annu Rev. Nutr., 27:19-40; Yorimitus et al., 2007, Trends Cell Biol., 17:279-285; Levine et al., 2008, Cell, 132:27-42; Kuma et al., 2004, Nature, 432:1032-36), clearing cell fate determinants and cell remodeling (Fimia et al., 2007, Nature, 447: 1121-25; Tsukamoto et al., 2008, Science, 321:117-120; Cecconi et al., 2008, Dev. Cell, 15:344-347). The results disclosed herein relate to a unique branch of the autophagy pathway that controls MBd levels, namely selective receptor-mediated autophagic degradation of MBds. We found that the autophagic receptor NBR1 (next to BRCA1 gene 1), binds the midbody protein, Cep55, directly linking the MBd to the autophagy degradation machinery. In normal (somatic and/or non-cancer) cells, NBR1-mediated autophagy degrades MBds, so they do not accumulate. NBR1 depletion increases MBds in these cells, as does inhibiting lysosomal/autolysosomal degradation. Importantly, NBR1 does not appear to affect global autophagy, suggesting that this unique branch of the autophagy pathway is selective or specific for MBd degradation.

In contrast, all cancer cells examined evaded autophagy, allowing MBds to accumulate. However, if MBd-specific autophagy is induced in cancer cells by increasing NBR1 expression and thus facilitating NBR1-Cep55 binding, MBds are efficiently eliminated. This is accompanied by a dramatic reduction in soft agar growth. Importantly, NBR1 expression appears to have no deleterious effect on normal cells as they have no/few MBds. This can define a new therapeutic strategy for selective neutralization/elimination of MBd+ cancer cells and/or cancer stem cells.

An exemplary human NBR1 protein sequence (GenBank NP_005890.2) is SEQ ID NO: 3.

Exemplary regions and sites in the NBR1 polypeptide sequence of SEQ ID NO: 3 are as follows:

```
Region     5..85
           /region_name="PB1_NBR1"
           /note="The PB1 domain is an essential part of NBR1
           protein, next to BRCA1, a scaffold protein mediating
           specific protein-protein interaction with both titin
           protein kinase and with another scaffold protein p62. A
           canonical PB1-PB1 interaction, which involves...; cd06396"
           /db_xref="CDD:99718"
Site       order(50,52,54,63)
           /site_type="other"
           /note="PB1 interaction site [polypeptide binding]"
           /db_xref="CDD:99718"
Region     215..259
           /region_name="ZZ_NBR1_like"
           /note="Zinc finger, ZZ type. Zinc finger present in
           Drosophila ref(2)P, NBR1, Human sequestosome 1 and related
           proteins. The ZZ motif coordinates two zinc ions and most
           likely participates in ligand binding or molecular
           scaffolding. Drosophila ref(2)P appears...; cd02340"
           /db_xref="CDD:30244"
Site       order(217,220,231,234,240,243,250,254)
           /site_type="other"
           /note="Zinc-binding sites [ion binding]"
           /db_xref"CDD:30244"
Site       order(217,220,240,243)
           /site_type"other"
           /note="zinc cluster 1 [ion binding]"
           /db_xref="CDD:30244"
Site       order(218,228,230,236,238)
           /site_type="other"
           /note="putative charged binding surface"
           /db_xref="CDD:30244"
Site       order(229,256,259)
           /site_type="other"
           /note="putative hydrophobic binding surface"
           /db_xref="CDD:30244"
Site       order(231,234,250,254)
           /site_type="other"
           /note="zinc cluster 2 [ion binding]"
           /db_xref="CDD:30244"
Region     542..636
           /region_name="ATG8 family protein-binding"
           /experiment="experimental evidence, no additional details
           recorded"
           /note="propagated from UniProtKB/Swiss-Prot (Q14596.3)"
Region     727..738
           /region_name="ATG8 family protein-binding"
           /experiment="experimental evidence, no additional details
           recorded"
           /note="propagated from UniProtKB/Swiss-Prot (Q14596.3)"
```

An exemplary NBR1 nucleic acid sequence (GenBank NM 005899.3) is SEQ ID NO: 4.

Stem Cells

Stem cells are primal cells that, upon division, can give rise both to another stem cell and a cell that will differentiate and ultimately die (see, e.g., Zipori, 2004, Nat. Rev. Genet. 5:873-878). Totipotent stem cells are produced from the fusion of an egg and sperm cell. Cells produced by the first few divisions of the fertilized egg cell are also totipotent. These cells can differentiate into embryonic and extraembryonic cell types. Pluripotent stem cells are the descendants of totipotent cells and can differentiate into cells derived from the three germ layers. Multipotent stem cells can produce only cells of a closely related family of cells (e.g., hematopoietic stem cells differentiate into red blood cells, white blood cells, or platelets). Unipotent cells can produce only one cell type, but have the property of self-renewal, which distinguishes them from non-stem cells. Stem cells are now believed to be present, though extremely scarce, in most tissues of the mammalian body, including the adult body. As demonstrated herein, MBds selectively accumulate in stem cells, induced pluripotent stem cells (iPSCs) and potential cancer 'stem cells' (CSCs) in vivo and in vitro. MBds appear to function in maintaining or enhancing the pluripotency of stem cells.

Reprogramming refers to a process by which a terminally differentiated cell can be restored to a state where it has the potential to differentiate into a new cell type. Numerous methods of reprogramming cells and producing induced pluripotent stem cells have been described. Such methods are reviewed in Wu et al., 2011, Nat. Cell Biol., 13:497-505; Hussein et al., 2011, Clin. Pharmacol. Ther., 89:741-745; Plath et al., 2011, Nat. Rev. Genet., 12:253-265; Gonzalez et al., 2011, Nat. Rev. Genet., 12:231-242; Sidhu, K S, 2011, Expert Opin. Biol. Ther., 11:569-579; Hanna et al., 2010, Cell, 143:508-525; and Stadtfeld et al., 2010, Genes Dev., 24:2239-63.

Putative markers of pluripotent stem cells include MBds, Alkaline phosphatase, Alpha-fetoprotein (AFP), Bone morphogenetic protein-4, Brachyury, Cluster designation 30 (CD30), Cripto (TDGF-1), GATA-4 gene, GCTM-2, Genesis, Germ cell nuclear factor, Hepatocyte nuclear factor-4 (HNF-4), Nestin, Neuronal cell-adhesion molecule (N-CAM), OCT4/POU5F1, Pax6, Stage-specific embryonic antigen-3 (SSEA-3), Stage-specific embryonic antigen-4 (SSEA-4), Stem cell factor (SCF or c-Kit ligand), Telomerase, TRA-1-60, TRA-1-81, and Vimentin. Additional markers, including lineage-specific markers, can be found at Appendix E: Stem Cell Markers. In Stem Cell Information [World Wide Web site]. Bethesda, Md.: National Institutes of Health, U.S. Department of Health and Human Services, 2009, Available at stemcells.nih.gov/info/scireport/appendixe.

Polypeptides

Exemplary agents that can be used in the methods described herein include polypeptides, e.g., antibodies, Cep55, NBR1, and fragments and analogs of any of the same.

In certain embodiments, the polypeptides include sequences substantially identical to all or a portion of a naturally occurring polypeptide. Polypeptides "substantially identical" to the a polypeptide sequence described herein have an amino acid sequence that is at least 65% (e.g., at least 75%, 80%, 85%, 90%, 95%, 98%, or 99%, e.g., 100%), identical to the amino acid sequences (e.g., SEQ ID NO:1 or SEQ ID NO:3). Furthermore, a polypeptide with up to 50, e.g., 1, 3, 5, 10, 15, 20, 25, 30, or 40, amino acid insertions, deletions, or substitutions, e.g., conservative amino acid substitutions will be useful in the compositions and methods described herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The percent identity between two amino acid sequences can be determined using the BLAST 2.0 program, which is available to the public at ncbi.nlm.nih.gov/BLAST. Sequence comparison is performed using the default parameters (BLOSUM 62 matrix, gap existence cost of 11, per residue gap cost of 1, and a lambda ratio of 0.85). The mathematical algorithm used in BLAST programs is described in Altschul et al., 1997, Nucleic Acids Research, 25:3389-3402.

Polypeptides useful in the methods described herein can be, but are not limited to, recombinant polypeptides and naturally occurring polypeptides. A polypeptide can be obtained from any human or mammalian species, and include alternatively spliced forms and other isoforms that have the disclosed activities. Non-human polypeptides with similarity to human Cep55 polypeptides have been identified in chimpanzees (e.g., GenBank Accession No. XP_521564.3), Sumatran orangutan (e.g., GenBank Accession No. XP_002821036.1), rhesus monkeys (e.g., GenBank Accession No. XP_001092020.1), white-cheeked gibbons (e.g., GenBank Accession No. XP_003255278.1), European rabbits (e.g., GenBank Accession No. XP_002718559.1), horses (e.g., GenBank Accession No. XP_001502506.1), cattle (e.g., GenBank Accession NP_001192690.1), dogs (e.g., GenBank Accession No. XP_850389.1), mice (e.g., GenBank Accession NP_001157834.1), and rats (e.g., GenBank Accession No. NP_001020817.1). Non-human polypeptides with similarity to human NBR1 polypeptides have been identified in chimpanzees (e.g., GenBank Accession No. XP_001155730.1), rhesus monkeys (e.g., GenBank Accession No. XP_001097043.2), white-cheeked gibbons (e.g., GenBank Accession No. XP_003279549.1), European rabbits (e.g., GenBank Accession No. XP_002719466.1), horses (e.g., GenBank Accession No. XP_001492040.1), cattle (e.g., GenBank Accession NP_001093837.1), dogs (e.g., GenBank Accession No. XP_537628.2), mice (e.g., GenBank Accession NP_032702.1), and rats (e.g., GenBank Accession No. NP_001019936.1). The person of ordinary skill can compare sequences between or among species to determine regions of the proteins most likely to be tolerant of modification.

Also useful in the new methods are fusion proteins in which a portion of a polypeptide is fused to an unrelated polypeptide (e.g., a marker polypeptide or purification tag) to create a fusion protein. For example, the polypeptide can be fused to a peptide tag to facilitate purification (e.g., a hexahistidine tag or a FLAG tag to facilitate purification of bacterially expressed polypeptides or to a hemagglutinin tag or a FLAG tag to facilitate purification of polypeptides expressed in eukaryotic cells). Also useful are, for example, polypeptides that include a first portion and a second portion; the first portion includes, e.g., a polypeptide, and the second portion includes, e.g., a detectable marker or a serum protein, e.g., an immunoglobulin constant region, or human serum albumin. In some embodiments, the fusion protein includes a cell-penetrating peptides (Johnson et al., 2011, Methods Mol. Biol., 683:535-551; Sawant et al., 2010, Mol. Biosyst., 6:628-640), pH-sensitive membrane peptide (pHLIP5) (Andreev et al., 2010, Mol. Membr. Biol., 27:341-352), or endosome-disruptive peptides (Nakase et al., 2010, Biopolymers, 94:763-770) to facilitate intracellular transduction of the polypeptide.

A polypeptide described herein can have one or more chemical modifications (e.g., posttranslational modifications) at one or more sites on the polypeptide, e.g., at the amino or carboxy terminus. Methods of chemical modification are well-known to those of skill in the art, and can be used to alter one or more properties, e.g., activity, stability, retention, or pharmacokinetics of the polypeptide. Exemplary modifications include glycosylation and PEGylation. Pegylation of polypeptides is known, e.g., as described in US 2006/0100144.

Also useful can be a peptidomimemtic version of a polypeptide described herein, functional fragment, or variant thereof. These polypeptides can be modified according to the methods known in the art for producing peptidomimetics. See, e.g., Kazmierski, W. M., ed., *Peptidomimetics Protocols*, Human Press (Totowa N. J. 1998); Goodman et al., eds., *Houben-Weyl Methods of Organic Chemistry: Synthesis of Peptides and Peptidomimetics*, Thiele Verlag (New York 2003); and Mayo et al., *J. Biol. Chem.*, 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as amino phosphonic acids and amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Also useful in the methods disclosed herein are nucleic acid molecules that encode polypeptide agents described herein, e.g., naturally occurring Cep55 or NBR1 polypeptides or forms of Cep55 or NBR1 polypeptides in which naturally occurring amino acid sequences are altered or deleted (e.g., fragments or analogs of Cep55 or NBR1). Certain nucleic acids can encode polypeptides that are soluble under normal physiological conditions. Polypeptides can be expressed (e.g., exogenously expressed) within a cell by any means known in the art. To generate cells that express polypeptides described herein, the cells can be transfected, transformed, or transduced using any of a variety of techniques known in the art. Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). Such techniques may result in stable or transient transformants. One suitable transfection technique is electroporation, which can be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation can be obtained from manufacturers.

Exemplary methods of administering polypeptides include introducing into a subject or a cell a nucleic acid that encodes a polypeptide described herein. In some embodiments, the nucleic acid that encodes the polypeptide is contained within a vector, e.g., as a virus that includes a nucleic acid that expresses the polypeptide. Exemplary viral vectors include adenoviruses (reviewed in Altaras et al., 2005, Adv. Biochem. Eng. Biotechnol., 99:193-260), adeno-associated viruses (reviewed in Park et al., 2008, Front. Biosci., 13:2653-59; see also Williams, 2007, Mol. Ther., 15:2053-54), parvoviruses, lentiviruses, retroviruses (reviewed in Tai et al., 2008, Front. Biosci., 13:3083-95), and the herpes simplex virus. Method of delivery of nucleic acids are reviewed in Patil et al., 2005, AAPS J., 7:E61-77, which is incorporated herein by reference in its entirety.

In some embodiments, a nucleic acid that expresses a polypeptide is administered directly to cancer cells or targeted to cancer cells.

An polypeptide described herein can be produced by any means known in the art, e.g., by chemical synthesis, recombinant methods, or isolation from cells that naturally produce the polypeptide. Methods of purification and isolation of molecules that include polypeptides are also well known to those of skill in the art.

Antibodies

In some embodiments, an antibody can be used in the methods and compositions described herein. Full length proteins or polypeptides can be used to raise antibodies useful in the methods described herein; such polypeptides can be produced by recombinant techniques or synthesized (see, for example, Stewart, "Solid Phase Peptide Synthesis," Freeman (1968); Sambrook et al., Molecular Cloning: A Laboratory Manual, Cold Spring Laboratory, Cold Spring Harbor, N.Y. (1989); Ausubel et al. (Eds.), Current Protocols in -Molecular Biology, John Wiley & Sons, New York, N.Y., 1999 and preceding editions; and U.S. Pat. No. 4,237,224). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a polypeptide described herein. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies are heterogeneous populations of antibody molecules that are contained in the sera of the immunized animals.

Antibodies for use in the new methods include polyclonal antibodies and, in addition, monoclonal antibodies, humanized or chimeric antibodies, single chain antibodies, Fab fragments, F(ab')2 fragments, CDR-grafted antibodies, deimmunized antibodies, molecules produced using a Fab expression library, and antigen binding fragments thereof. In some embodiments, the antibody is a bispecific antibody.

An IgG type bispecific antibody can be secreted by a hybrid hybridoma (quadroma) formed by fusing two types of hybridomas that produce IgG antibodies (Milstein C et al., Nature 1983, 305: 537-540). It can also be secreted by introducing into cells genes of the L chains and H chains that constitute the two IgGs of interest (a total of four types of genes) for co-expression. In this case, by appropriately substituting amino acid(s) in the CH3 region of an H chain, it is possible to preferentially secrete IgGs that have a heterologous combination of H chains (Ridgway, J B et al. Protein Engineering 1996, 9: 617-621, Merchant, A M et al. Nature Biotechnology 1998, 16: 677-681).

A bispecific antibody can also be prepared by chemically cross-linking Fab's. A bispecific F(ab')2 can be produced, for example, by maleimidating a Fab' prepared from one antibody with o-PDM (ortho-phenylenedi-maleimide) and reacting the product with a Fab' prepared from another antibody, so as to cross-link Fab's derived from different antibodies (Keler T et al. Cancer Research 1997, 57: 4008-4014). Further, a method for chemically connecting antibody fragments such as a Fab'-thionitrobenzoic acid (TNB) derivative and Fab'-thiol (SH) is also known (Brennan M et al. Science 1985, 229: 81-83).

Instead of cross linkage, a leucine zipper derived from Fos and Jun or the like can be used. Although Fos and Jun also form a homodimer, their preferential heterodimer formation is utilized. A Fab' added with a Fos leucine zipper and a second Fab' added with a Jun leucine zipper is expressed for preparation. By mixing and reacting monomeric Fab'-Fos and Fab'-Jun, which have been reduced under mild conditions, a bispecific F(ab')2 can be formed (Kostelny S A et al. J. of Immunology, 1992, 148: 1547-53). This method is not limited to Fab' and can also be applied to scFv, Fv, etc.

A bispecific antibody can also be prepared in a form of diabody. A bispecific diabody is a heterodimer comprising two crossover scFv fragments. That is, a bispecific diabody can be prepared by constructing a heterodimer using VH(A)-VL(B) and VH(B)-VL(A), which have been formed by connecting VH and VL derived from two types of antibodies: A and B, with a relatively short linker of about 5 amino acid residues (Holliger P et al. Proc. of the National Academy of Sciences of the USA 1993, 90: 6444-6448).

In this case, construction of a bispecific diabody of interest can be promoted by performing appropriate amino acid substitutions (knobs-into-holes: Zhu Z et al. Protein Science. 1997, 6: 781-788) so as to link two types of scFv's with a flexible and relatively long linker of about 15 amino acid residues (a single-chain diabody: Kipriyanov S M et al. J. of Molecular Biology. 1999, 293: 41-56).

sc(Fv)2 which can be prepared by linking two types of scFv's with a flexible and relatively long linker of about 15 amino acid residues can also become a bispecific antibody (Mallender W D et al. J. of Biological Chemistry, 1994, 269: 199-206).

A modified antibody may be, for example, an antibody that binds to various molecules such as polyethylene glycol (PEG). In the modified antibodies of the present invention, substances to be bound are not limited. Such modified antibodies can be obtained by chemically modifying the antibodies obtained. These methods have already been established in this field.

Monoclonal antibodies (mAbs), which are homogeneous populations of antibodies to a particular antigen, can be prepared using the polypeptides described above and standard hybridoma technology (see, for example, Kohler et al., Nature, 256:495, 1975; Kohler et al., Eur. J. Immunol., 6:511, 1976; Kohler et al., Eur. J. Immunol., 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al. (Nature, 256:495, 1975, and U.S. Pat. No. 4,376,110); the human B-cell hybridoma technique (Kosbor et al., Immunology Today, 4:72, 1983; Cole et al., Proc. Natl. Acad. Sci. USA, 80:2026, 1983); and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. Hybridomas producing mAbs may be cultivated in vitro or in vivo. The ability to produce high titers of mAbs in vivo makes this a particularly useful method of production.

In some embodiments, antibodies are produced using fragments of the polypeptides that lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

In other embodiments, techniques developed for the production of "chimeric antibodies" (Morrison et al., Proc. Natl. Acad. Sci. USA, 81:6851, 1984; Neuberger et al., Nature, 312:604, 1984; Takeda et al., Nature, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Generally, partially human antibodies and fully human antibodies have a longer half-life within the human body than other antibodies. Accordingly, lower dosages and less frequent administration are often possible than with non-human antibodies. Modifications such as lipidation can be used to stabilize antibodies and to enhance uptake and tissue penetration (e.g., into the brain). A method for lipidation of antibodies is described by Cruikshank et al. (J. Acquir. Immune Defic. Syndr., 14:193, 1997).

Alternatively, techniques described for the production of single chain antibodies (U.S. Pat. Nos. 4,946,778, 4,946,778, and 4,704,692) can be adapted to produce single chain antibodies against proteins, or fragments thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science, 246:1275, 1989) to allow rapid and easy identification of monoclonal Fab fragments with the desired specificity.

Antibodies to polypeptides can, in turn, be used to generate anti-idiotype antibodies using techniques well known to those skilled in the art (see, e.g., Greenspan et al., FASEB J., 7:437, 1993; Nissinoff, J. Immunol., 147:2429, 1991). For example, antibodies that bind to a polypeptide and competitively inhibit the binding of a binding partner of that polypeptide (e.g., Cep55 and NBR1) can be used to generate anti-idiotypes that resemble a binding partner binding domain of the protein and, therefore, bind and neutralize a binding partner of the protein. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also contemplated (Green et al., Nature Genetics, 7:13-21, 1994; see also U.S. Pat. Nos. 5,545,806 and 5,569,825).

In certain embodiments, an antibody described herein may be an antibody that is expressed as an intracellular protein. Such intracellular antibodies are also referred to as intrabodies and may include an Fab fragment, or preferably include a scFv fragment (see, e.g., Lecerf et al., Proc. Natl. Acad. Sci. USA 98:4764-49 (2001). The framework regions flanking the CDR regions can be modified to improve expression levels and solubility of an intrabody in an intracellular reducing environment (see, e.g., Worn et al., J. Biol. Chem. 275:2795-803 (2000)). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., Mol. Cell Biol. 15:1182-91 (1995); Lener et al., Eur. J. Biochem. 267:1196-205 (2000)). An intrabody may be introduced into a cell by a variety of techniques available to the skilled artisan including via a gene therapy vector, or a lipid mixture (e.g., Provectin.TM. manufactured by Imgenex Corporation, San Diego, Calif.), or according to photochemical internalization methods.

Artificial Transcription Factors

In some embodiments, expression of a polypeptide described herein (e.g., Cep55 or NBR1) can be modulated (e.g., increased or decreased) using an artificial transcription factor, e.g., a small molecule or a protein comprising a zinc finger (Sera T., 2009, Adv. Drug Deliv. Rev., 61:513-526) or transcription activator like (TAL) (Scholze et al., 2010, Virulence, 1:428-432) domain. Artificial transcription factors can be designed to target and modulate the expression of the Cep55 or NBR1 gene. Artificial transcription factors and their production and uses are reviewed, e.g., in Rodriguez-Martinez et al., 2010, Biochim. Biophys. Acta, 1799:768-774; Sera T., 2009, Adv. Drug Deliv. Rev., 61:513-526; Blancafort et al., 2008, Comb. Chem. High Throughput Screen., 11:146-158; Koh et al., 2007, ACS Chem. Biol., 2:599-601).

Inhibitory Nucleic Acids

In some embodiments, expression of NBR1 can be inhibited using an inhibitory nucleic acid, e.g., siRNA, miRNA, piRNA, antisense, ribozyme, or aptamer.

RNA interference (RNAi) is a process whereby double-stranded RNA (dsRNA) induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev.:12, 225-232 (2002); Sharp, Genes Dev., 15:485-490 (2001); Valencia-Sanchez et al. Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411: 494-498 (2001)), by microRNA (miRNA), functional small-hairpin RNA (shRNA), or other dsRNAs which are expressed in vivo using DNA templates with RNA polymerase II or III promoters (Zeng et al., Mol. Cell 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002).)

The methods described herein can use, e.g., dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA (e.g., SEQ ID NO:4), and the other strand is complementary to the first strand. The dsRNA molecules can be chemically synthesized, or can transcribed be in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the disclosure includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothiate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004))

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety of the particle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using 3H, 32P, or other appropriate isotope.

siRNA duplexes can be expressed within cells from recombinant DNA constructs, including mammalian Pol II and III promoter systems (e.g., H1, U1, or U6/snRNA promoter systems (Denti et al. (2004), supra; Tuschl (2002), supra; capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, an mRNA to be targeted by the siRNA generated from the engineered RNA precursor can be depleted from the cell or organism, leading to a decrease in the concentration of the protein encoded by that mRNA in the cell or organism.

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Target gene expression can be inhibited by targeting nucleotide sequences complementary to a regulatory region, e.g., promoters and/or enhancers) to form triple helical structures that prevent transcription of the target gene in target cells. See generally, Helene, C. Anticancer Drug Des. 6:569-584 (1991); Helene, C. Ann. N.Y. Acad. Sci. 660:27-36 (1992); and Maher, Bioassays 14:807-815 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target-protein encoding nucleic acid can include one or more sequences complementary to the nucleotide sequence of a target cDNA disclosed herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-18 (1993).

Carriers

In some embodiments, a composition that includes a polypeptide, antibody, or nucleic acid described herein can also include a carrier, e.g., for targeting the agent to a specific cell or cell type or for aiding in intracellular transduction of the agent.

For example, the carrier can be a lipid-based carrier (e.g., a liposome) (Musacchio et al., 2011, Front. Biosci., 1388-1412), nanoparticle (see, e.g., WO 2007/133807; WO 2008/097609; WO 2010/120385; WO 2011/084620; Kim et al., "Nanoparticle delivery of a peptide targeting EGFR signaling," J Control Release, 2011 Aug. 17; Youns et al., 2011, Curr. Drug Targets, 12:357-365), or other composition (Nguyen et al., "Targeting ligand-functionalized and redox-sensitive heparin-Pluronic nanogels for intracellular protein delivery," Biomed. Mater., 2011 Aug. 18;6(5):055004; Kamkaew et al., "Cationic polyfluorenes for intracellular delivery of proteins," Org. Biomol. Chem., 2011 Aug. 16).

In some embodiments, the carrier can include one or more agents for targeting the polypeptide, antibody, or nucleic acid to a specific cell or cell type. In some embodiments, the targeting agent is a polypeptide, antibody, or aptamer, e.g., that binds to a protein found on the membrane of a target cell or cell type. Targeting of carriers and targeting agents are described, e.g., in WO 2007/137117; WO 2008/105773; WO 2008/124632; WO 2008/124639.

In some embodiments, the carrier can include one or more agents for aiding in intracellular transduction of the polypeptide, antibody, or nucleic acid, e.g., a cell-penetrating peptide (Johnson et al., 2011, Methods Mol. Biol., 683:535-551; Sawant et al., 2010, Mol. Biosyst., 6:628-640), pH-sensitive membrane peptide (pHLIP5) (Andreev et al., 2010, Mol. Membr. Biol., 27:341-352), or endosome-disruptive peptide (Nakase et al., 2010, Biopolymers, 94:763-770).

Cancers

The new methods can be used to diagnose and treat several types of cancer, e.g., melanomas, thyroid cancers (e.g., papillary thyroid carcinoma, anaplastic thyroid carcinoma, follicular carcinoma, follicular adenoma), colorectal cancers, lung cancers (e.g., adenocarcinoma, nonsmall cell lung cancer), lymphomas (e.g., non-Hodgkin lymphoma), multiple myeloma, leukemias, breast cancers, ovarian cancers, gastric cancers, bladder cancers, pancreatic cancers, gall bladder cancers, bile duct cancers, and other carcinomas. Methods of diagnosing cancers are well known to those of skill in the art. In some embodiments, the new methods can be useful for any type of tumor, cancer, or neoplasm that has increased numbers of MBds or is dependent for growth and/or survival upon increased numbers of MBds. In some embodiments, a method described herein, e.g., a method of treating a cancer in a subject, can include a step of identifying the subject as having, suffering from, or being at risk for a cancer.

Pharmaceutical Formulations

The agents described herein (all of which can be referred to herein as "active compounds"), can be incorporated into pharmaceutical compositions. Such compositions typically include the active compound and a pharmaceutically acceptable carrier or excipient. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

There are a number of methods by which the new compositions for use in the new methods can be delivered to subjects, in general, and to specific cells or tissue in those subjects, in particular. For example, an agent described herein can be injected into a subject or a tissue of the subject. In another example, a vector (e.g., a plasmid or virus) encoding an agent can be introduced into a cell or tissue of the subject. The vector would then enter the cell or cells in that tissue and express the agent. Delivery specificity of such plasmids can be enhanced by associating them with tumor-, organ- or tissue-specific affinity, so that they preferentially enter specified cell types. Methods of expressing proteins for tumor therapy are described, e.g., in Cross and Burmester, 2006, Clin. Med. Res., 4:218-227; Lejuene et al., 2007, Expert Rev. Anticancer Ther. 7:701-713; and Bloquel et al., 2004, J. Gene Med., 6:S11-S23.

Compounds and their physiologically acceptable salts and solvates can be formulated for oral, topical, buccal, parenteral or rectal administration or administration by inhalation or insufflation (either through the mouth or the nose).

The compounds will generally be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use. Where the compositions are intended for use in a specific treatment area, the compositions can be administered by one or more local injections into the tumor site to diminish as much as possible any side effects relating to the compound's activities outside of the treatment area.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt. A depot preparation can include embedded or encapsulated cells or tissue that secrete an agent, which can be administered, e.g., by implantation or by intramuscular injection.

The compositions can, if desired, be presented in a pack or dispenser device that can contain one or more unit dosage forms containing the active ingredient. The pack can, for example, include metal or plastic foil, such as a blister pack. The pack or dispenser device can be accompanied by instructions for administration.

The therapeutic compositions disclosed herein can also contain a carrier or excipient, many of which are known to skilled artisans. Methods for making such formulations are well known and can be found in, for example, Remington: The Science and Practice of Pharmacy, University of the Sciences in Philadelphia (USIP), 2005.

The compositions can also be formulated for intracellular delivery of the active compounds, using methods known in the art. For example, the compositions can include liposomes or other carriers that deliver the active compound across the plasma membrane. Vesicles that are covered with cell-penetrating peptides, such as Tat or Antennapedia, can also be used. A number of other methods for enhancing intracellular delivery are familiar to those of skill in the art.

It is recognized that the pharmaceutical compositions and methods described herein can be used independently or in combination with one another. That is, subjects can be administered one or more of the pharmaceutical compositions, e.g., pharmaceutical compositions that include an agent, subjected to one or more of the therapeutic methods described herein, or both, in temporally overlapping or non-overlapping regimens. When therapies overlap temporally, the therapies can generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody described herein) which can, in one embodiment, be conjugated or linked with a therapeutic agent, a cytotoxic agent, an imaging agent, or the like.

Effective Doses

Toxicity and therapeutic efficacy of an agent described herein can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Inhibitors that exhibit large therapeutic indices are preferred. While inhibitors that exhibit toxic side effects can be used, care can be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the new methods, the therapeutically effective dose can be estimated initially from cell culture assays. A dose can also be calculated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

EXAMPLES

Example 1

Post-Mitotic Midbodies Accumulate within Cells

Figure 1:
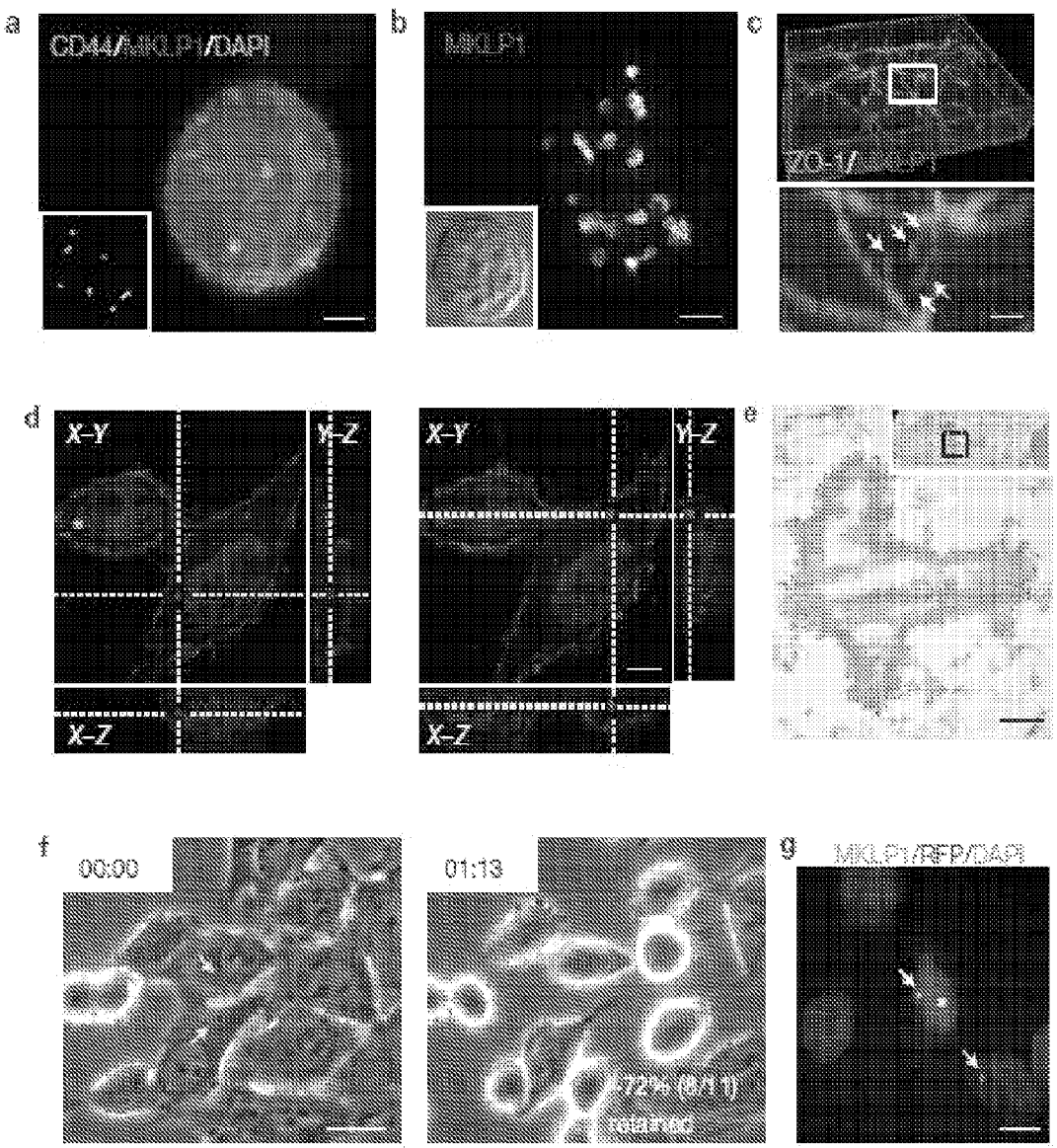
FIG. 1. MBds accumulate within cells. (a, b) Multiple MBds associate with a PC3 cell (a) and a B-lymphoblast (b). Insets (a) MBd labeling and (b) merged phase-contrast image with MBd labeling to show cell boundaries. MKLP1, MBd marker (a, b; red); CD44, membrane (a; green); DAPI, DNA (a; blue). Bar, 5 µm (a) and 2 µm (b). (c, d) Three-dimensional reconstruction of polarized cells in a monolayer (c) and a HeLa cell (d) show intracellular MBds. (c) ZO-1, tight junction; MKLP1, MBds. Bar, 2 µm. Enlargement (c, bottom) of box (c, top) shows five MBds (arrows). (d) Wheat germ agglutinin, plasma membrane (red); MKLP1-GFP, MBds (green); DAPI, DNA (blue). Bar, 5 µm. (e) Electron micrograph of a MBd in a permeabilized MCF-7 cell showing immunogold labeling with MKLP1 antibodies. Inset, lower magnification of the MBd (boxed) in cell; nucleus, right. Bar, 200 nm. (f) Time-lapse images during extracellular trypsin treatment of HeLa cells show retention of most MBds (MKLP1-GFP, red). Two MBds (yellow arrows) are lost upon treatment, suggesting digestion and/or dissociation. Time (hr: min) post-trypsin. Bar, 5 µm. (g) Two-day co-cultures of HeLa cell expressing either MKLP1-GFP (MBd marker) or cytosolic RFP. Green MBds (arrows) associated with red cells (asterisk) indicate post-mitotic transfer of MBds between cells. Bar, 10 µm.

Multiple MBds were observed in subpopulations of cells by immunofluorescence (IF), but their precise location was unclear (up to 20; FIG. 1a, b). Three-dimensional reconstruction of immunofluorescent images revealed multiple MBds inside polarized and nonpolarized cells (FIG. 1c, d). Immuno-electron microscopy confirmed this localization and revealed ultrastructural features characteristic of MBds (FIG. 1e) (Mullins et al., 1977, J. Cell Biol., 73:672-684; Dubreuil et al., 2007, J. Cell Biol., 176:483-495). About 70% of cell-associated MBds were trypsin-resistant, suggesting that they were intracellular (FIG. 1f). This intracellular localization of MBds suggested that they might accumulate in cells through successive divisions.

MBds were also released from cells. In 2-day co-cultures of HeLa cells stably expressing either monomeric RFP (cytoplasmic marker) or MKLP1-GFP (MB marker), about 7% of MKLP1-GFP+ MBds associated with RFP+ cells (FIG. 1g). Such free MBds were also generated by other cell types (e.g. human adult fibroblasts, HeLa; 1-10%). These observations resolve the conflict of previous studies suggesting that MBds are either retained and degraded (Gromley et al., 2005, Cell, 123:75-88; Goss et al., 2008, J. Cell Biol., 181:1047-54; Pohl et al., 2009, Nat. Cell Biol., 11:65-70) or released as remnants after abscission (Mullins et al., 1977, J. Cell Biol., 73:672-684). We show that MBds accumulate in some cells (FIG. 1a-d) but not others.

Example 2

MBds are Inherited by the Cell with the Older Centrosome

Figure 2:
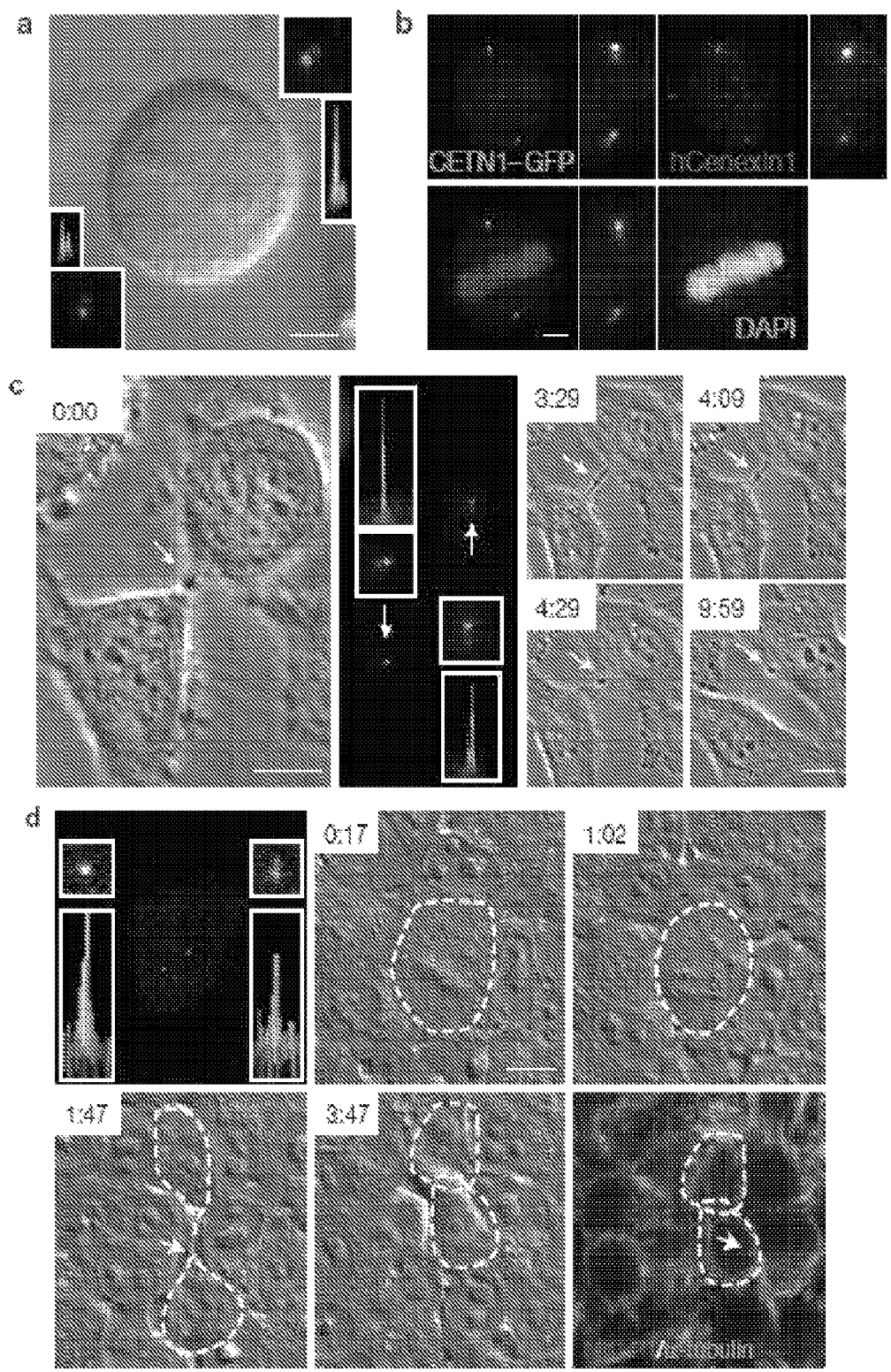
FIG. 2. MBds are preferentially inherited by the cell with the older centrosome. (a) CETN1-GFP signal is brighter in upper centrosome/spindle pole of a mitotic spindle. The merged DIC image with CETN1-GFP labeling at two centrosomes shows metaphase chromosome. Insets (lower left, upper right), enlargement and semi-quantitative integrated intensity profile of centrioles. Bar, 5 µm. (b) The brighter CETN1-GFP signal represents the older centrosome as it co-stains more intensely for hCenexin1 and remains more intense throughout cell division. Bar, 5 µm. Lower left, merge. (c, d) Time-lapse images show that the mitotic MB is preferentially inherited by the daughter cell with the older centrosome in HeLa cells (c) and hESCs (d). Cells were imaged at the indicated times (hr:min) from telophase by phase-contrast microscopy (c) and from metaphase by DIC microscopy (d). Middle panel of (c) and left panel of (d), CETN1-GFP at centrosomes; enlargements and integrated intensity profiles show the daughter cell having the older centrosome (c, upper; d, lower) inherits the MBd (Time-lapse images: 9:59 in c; lower right image in d). Mitotic MB and MBds (c, d; arrows). MKLP1, MBd marker (red); α-tubulin, mitotic MB and cell boundary marker (green); DAPI, DNA (blue). Bars, 10 µm (c, d).

In G1, the centrosome contains one mother centriole (MC) and one daughter centriole (DC) (Doxsey et al., 2005, Annu Rev. Cell Dev. Biol., 21:411-434). After centriole duplication, three generations of centrioles are present: an older mother, a younger mother and two new daughters (Doxsey et al., 2005, Annu Rev. Cell Dev. Biol., 21:411-434; Anderson et al., 2009, Curr. Biol., 19:1498-1502). The centrosome with the older MC is termed the older centrosome (Yamashita et al., 2007, Science, 315:518-521; Wang et al., 2009, Nature, 461:947-955). GFP-tagged centrin1 (CETN1-GFP) (Piel et al., 2000, J. Cell Biol., 149:317-330) expressed in mitotic HeLa cells was brightest at one of the four centrioles (92.2% of cells, n=116; FIG. 2a) and turned over very slowly (FRAP $t_{1/2}$-4 hours; Wang et al., 2009, Nature, 461:947-955). The brightest centriole remained so from metaphase to late cytokinesis (91.3% of cells, n=46), suggesting that it was the older MC. This was confirmed by staining with the older centrosome marker, hCenexin1 (Anderson et al., 2009, Curr. Biol., 19:1498-1502) (~90% of HeLa and MCF-7 cells, n=143 and n=347, respectively; FIG. 2b). Several other centriole antigens also showed intrinsic age-related differences in labeling.

Using CETN1-GFP to identify the older MC; bright-field imaging to follow MB dynamics in living cells; and immunofluorescence to confirm MBd inheritance, we determined that MBds were preferentially inherited by the cell with the older centrosome. This was observed in pluripotent human embryonic stem cells (hESCs; 83.3% of H9, n=18; FIG. 2d), immortalized somatic cells (91.3% of hRPE-1, n=23) and cancer cells (U2OS: 84.6%, n=13; HeLa: 75.0%, n=24; FIG. 2c). This demonstrates that MBds are asymmetrically transferred to the daughter cell with the older centrosome in several cell types.

Example 3

MBds Accumulate in Stem Cells In Vivo

Figure 3:
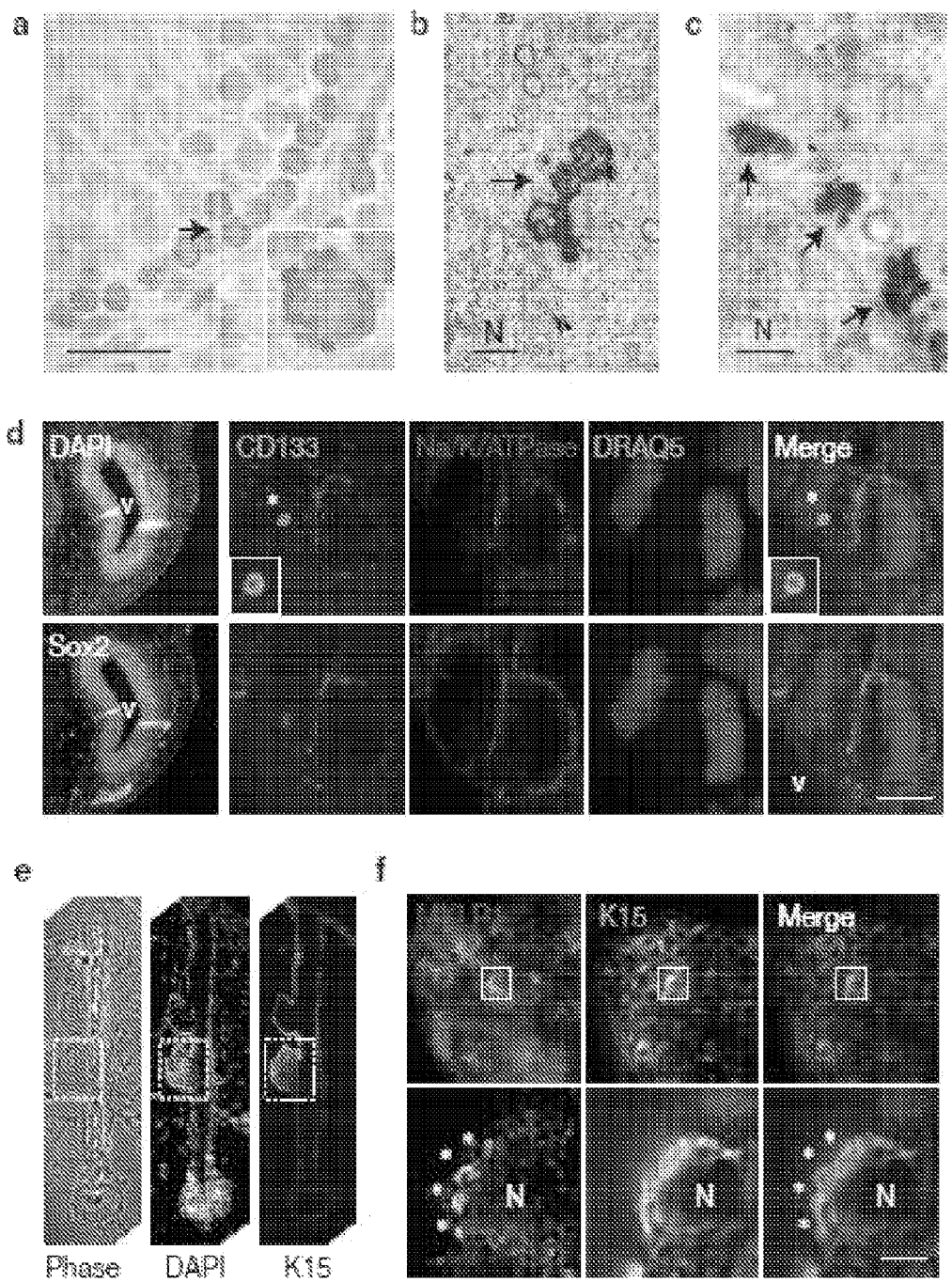
FIG. 3. MBds accumulate in stem cells in vivo and in vitro. (a) Histological section through mouse seminiferous tubules labeled for MKLP1 shows several MKLP1+ puncta in cells of the basal layer where stem cells reside. Bar, 20 µm. Inset, enlargement of the cell (arrow) (b, c) Electron micrographs of mitotic MB (b, arrow) and multiple MB-like structures in interphase cells with similar shape and size in a juxtanuclear position (c, arrows) in basal cells of mouse seminiferous tubules. N, nucleus. Bars, 1 μm. (d) Representative planes of a neural progenitor cell in the ventricular zone (Sox2+, left-bottom panel) of an E13.5 mouse brain show that an intracellular MBd (asterisk) is associated with the ventricle-facing daughter in the asymmetrically dividing cell (top row). The bottom row emphasizes the position of paired chromosomes in a dividing anaphase cell. CD 133, MB/MBd marker (green); Na-K-ATPase, cell-border marker (red); DRAQ5, DNA (blue); DAPI, DNA. Ventricle (V). Bar, 5 μm. Note that abscission occurs apically in these cells. (e) A histological section through a hair follicle (left, phase-contrast microscopy) stained for the stem cell marker keratin 15 to identify the bulge region (dotted box), the stem cell niche. DNA stain (DAPI) and the phase-contrast image show full follicle architecture. (f) Upper panels show MBd-accumulating cells in the bulge region (boxed) colabeled with K15 and MKLP1. Enlargements (lower panels) of the boxed region highlight a cell with four MBds (asterisks). N, nucleus. Bar, 5 μm. (g-i) Quantitative analysis and representative images show a decrease in MBd-accumulating cells (percentage, bottom) upon the differentiation of pluripotent stem cells (g, H1-OGN) to fibroblast-like cells (h, dH1f), and an increase in MBd-accumulating cells after reprogramming differentiated cells (h) to induced pluripotent stem cells (I, dH1f-iPS). MKLP1, MBds; ZO-1, tight junctions; α-tubulin, microtubules; Aurora B, MBs. Bar, 10 μm.
Figure 3:
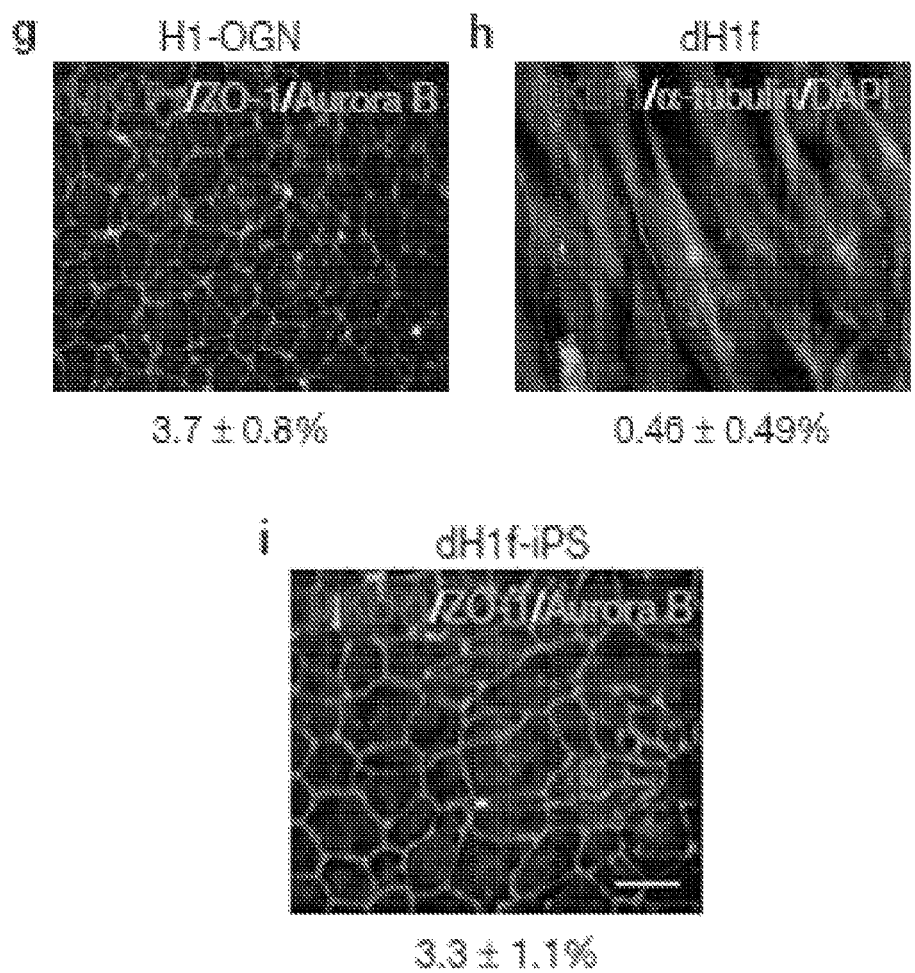

To address whether MBds were found in stem cell niches, we determined the localization of MBds in human and mouse tissues. In seminiferous tubules of testes, MBds were confined to the basal compartment, the site of germline stem cells and their mitotic progeny (both capable of self-renewal (Oatley et al., 2008, Annu Rev. Cell Dev. Biol., 24:273-286; Barroca et al., 2009, Nat. Cell Biol., 11:190-196) (FIG. 3a, up to 8 puncta/cell, 5-μm section). Electron microscopy also revealed multiple cytoplasmic structures with features characteristic of MBds within these cells (FIG. 3b, c).

In the ventricular zone (VZ, Sox2+; Bilgüvar et al., 2010, Nature, 467:207-210) of embryonic mouse brains, CD133-labeled MBds were associated with neural progenitors (Marzesco et al., 2005, J. Cell Sci., 118:2849-58; Dubreuil et al., 2007, J. Cell Biol., 176:483-495) (FIG. 3d). During asymmetric divisions, intracellular MBds were usually found in ventricle-facing daughter cells (progenitors; 75%, n=8) and not in daughters with presumed committed fates (Wang et al., 2009, Nature, 461:947-955). MBds in the human hair follicle were also confined to a subpopulation of cells in the stem cell niche, the bulge (Morris et al., 2004, Nat. Biotechnol., 22:411-417), suggesting distinct properties of this subpopulation (FIG. 3e, f). MBds were also enriched in β1-integrin+ (Conboy et al., 2010, Methods Mol., Biol., 621:165-173) mouse skeletal muscle progenitors (SMPs; 4-fold) over non-SMP cells. These observations suggested that MBds were selectively retained and accumulated during successive stem cell divisions in vivo.

Example 4

MBds Accumulate in Stem Cells in vitro

To rigorously test the idea that MBds are selectively inherited by stem cells, we examined MBd fate during stem cell differentiation and somatic cell reprogramming. MBd 'accumulation' was assessed by counting cells with >1 MBd, as all cells can transiently acquire one MBd after abscission (below). MBd-accumulation decreased ~8-fold upon differentiation of hESCs (H1-OGN) to fibroblast-like cells (dH1f; FIG. 3g, h). Differentiation was judged by loss of embryonic stem cell markers (Oct4, Sox2, Klf4, Nanog) and gain of the CD13 differentiation marker (Park et al., 2008, Nature, 451: 141-146; Chan et al., 2009, Nat. Biotechnol., 27:1033-37). In contrast, MBd-accumulation increased ~7-fold after reprogramming dH1f cells to iPSCs (Park et al., 2008, Nature, 451:141-146; Zwaka et al., 203, Nat. Biotechnol., 21:319-321) (dH1f-iPS; FIG. 3h, i). We conclude that MBd-accumulation in vitro reflects that observed in vivo, and can be manipulated by altering the potency status of cells.

Example 5

MBd Accumulation is Enhanced in Tumor-Derived Cells

Figure 4:
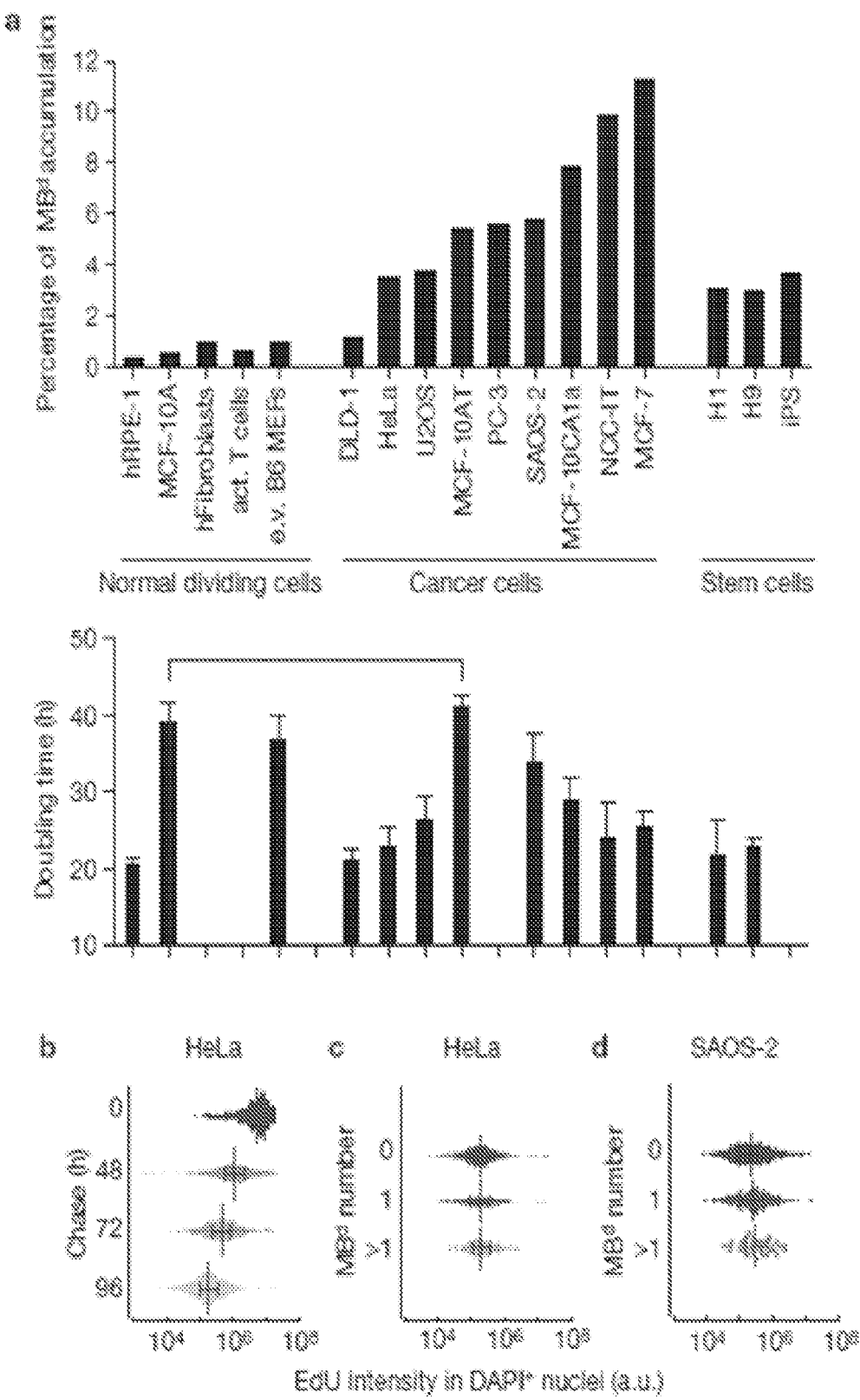
FIG. 4. MBd-accumulation is high in stem cells and subpopulations of cancer cells and does not correlate with cell doubling time. (a) Percent of cells that accumulate MBds (>1) in a range of different cell types, as indicated. Below, doubling-times of representative cell lines aligned with MBd-accumulation data. Horizontal line, cell lines with different MBd-accumulation potential (14-fold) but similar doubling time. (b) Cells pulse-chased with EdU show a decrease in EdU intensity (x-axis) over time (y-axis), reflecting dilution of dye after cell divisions. Red dashed lines and bars, median and interquartile range, respectively. (c) After a 96 hr chase period, EdU levels were compared in cells with different MBd numbers (y-axis). A representative graph of triplicate experiments is presented. Similar profiles of EdU intensities suggest similar division rates in HeLa cells (p=0.2101, one-way ANOVA, cells analyzed: 2008) (d) Representative experiment as in (c) using SAOS cells. Similarly, no significant differences were noted (p=0.5609, one-way ANOVA, cells analyzed: 1960).

We next examined differences in MBd-accumulation among cell lines derived from stem cells, normal dividing cells and cancer cells (FIG. 4a). MBd-accumulation was low in primary and telomerase-immortalized normal cells and significantly higher in hESCs and iPSCs (~7-fold on average; FIG. 4a). Most cancer cells exhibited even higher levels of MBd-accumulation. For example, MBd-accumulation in tumorigenic MCF-10AT and MCF-10CA1a cells was much higher than in the normal MCF-10A parental line. The common ability of stem cells and cancer cells to accumulate MBds, express stem cell markers (Visvader et al., 2008, Nat. Rev. Cancer, 8:755-768) and possess stem cell properties (O'Brien et al., 2007, Nature, 445:106-110; Pece et al., 2010, Cell, 140:62-73) suggests a relationship between MBd-accumulation, tumorigenicity and cancer 'initiating' or 'stem' cells defined by the CSC theory (Pardal et al., 2003, Nat. Rev. Cancer, 3:895-902).

Example 6

MBd Accumulation does not Correlate with Cell Proliferation Rate

A simple explanation for cell type-specific differences in MBd-accumulation is variability in proliferation rates. Slower division rates could allow more time for MBd degradation, as recently proposed (Pohl et al., 2009, Nat. Cell Biol., 11:65-70). However, we observed no correlation between population doubling-time and MBd-accumulation (FIG. 4a). It was still possible that MBd-accumulating cells cycled faster than the bulk population. However, a cohort of cells pulse-labeled with EdU (Salic et al., 2008, Proc. Natl. Acad. Sci. USA, 105:2415-20) showed a proportional decrease in EdU intensity, reflecting dilution of dye after successive divisions (FIG. 4b) and indicating that MBd-accumulating and non-accumulating subpopulations had similar cycling rates (FIG. 4c, d).

Example 7

MBd-Accumulating Cells Evade Membrane Encapsulation of MBds

Figure 5:
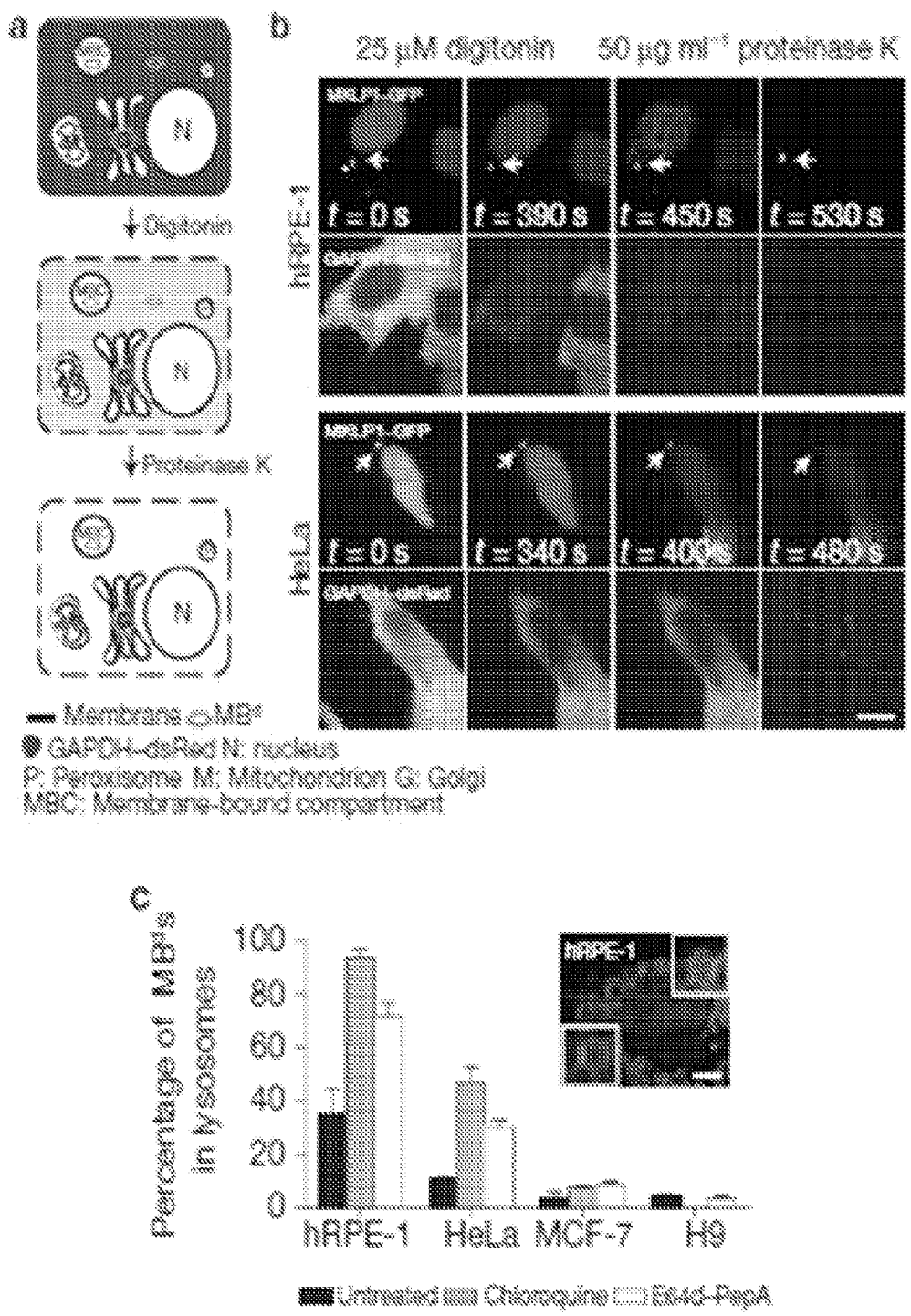
FIG. 5. MBds in stem and cancer cells evade membrane encapsulation and lysosomal degradation. (a) Depiction of fluorescence protease protection (FPP) assay. Digitonin selectively permeabilizes the plasma membrane but not internal membranes. Proteinase K degrades cytoplasmic components but membranous compartments remain intact. Under these conditions, MKLP1-GFP-labeled MBds (blue circle) in the cytoplasm will be degraded whereas those inside membrane-bound compartments (MBCs) will not. (b) MBds in MBd-poor hRPE-1 cells are largely protected (~90% in membranous compartments, cells analyzed=10), whereas most MBds in HeLa cells are not (~27%, cells analyzed: 11), and are thus degraded in cytoplasm. Bar, 5 μm. (c) Graph depicting the presence of MBds in lysosomes upon chloroquine or E64d/pepstatin A (E64d/PepA) inhibition in hRPE-1 and HeLa cells, but not in MCF-7 and H9 hESCs. Chloroquine treatment of H9 hESCs is not included as it caused differentiation and cell death. A representative image of hRPE-1 cells inhibited by chloroquine is shown depicting two MBds inside lysosomes. MKLP1 and LAMP2 are used as MBd (red) and lysosome (green) markers, respectively. DAPI, DNA (blue). n=100 MBds/treatment in each of the biological triplicates. Bar, 5 μm. (d) Graph showing the percent of MBd+ cells (MBd levels), the percent of MBds within lysosomes, and the percent of cells exiting cytokinesis following synchronization. MKLP1 and LAMP2 are used as markers as in (c). Note that MBds are transferred into only one of the two nascent daughter cells after abscission (FIG. 2d), so a 50% maximum will be expected for MBd+ cells. The peak of MBds transferred to cells is 3 hours after plating followed by a peak of MBds entering lysosomes at 7 hours. (e) Both chloroquine and E64d/PepA treatments increase the percent of MBd+ cells in hRPE-1 cells and HeLa cells (chloroquine: p=0.0021 and p=0.0187, respectively; E64d/PepA: p=0.0022 and p=0.0043, respectively; n=3 for all experiments). In contrast, lysosomal inhibition has no detectable effect on hESCs (H1, H9) and MCF-7 cancer cells. Data are presented as mean±s.d. (c-e), except mean±s.e.m. in hESCs (e).
Figure 5:
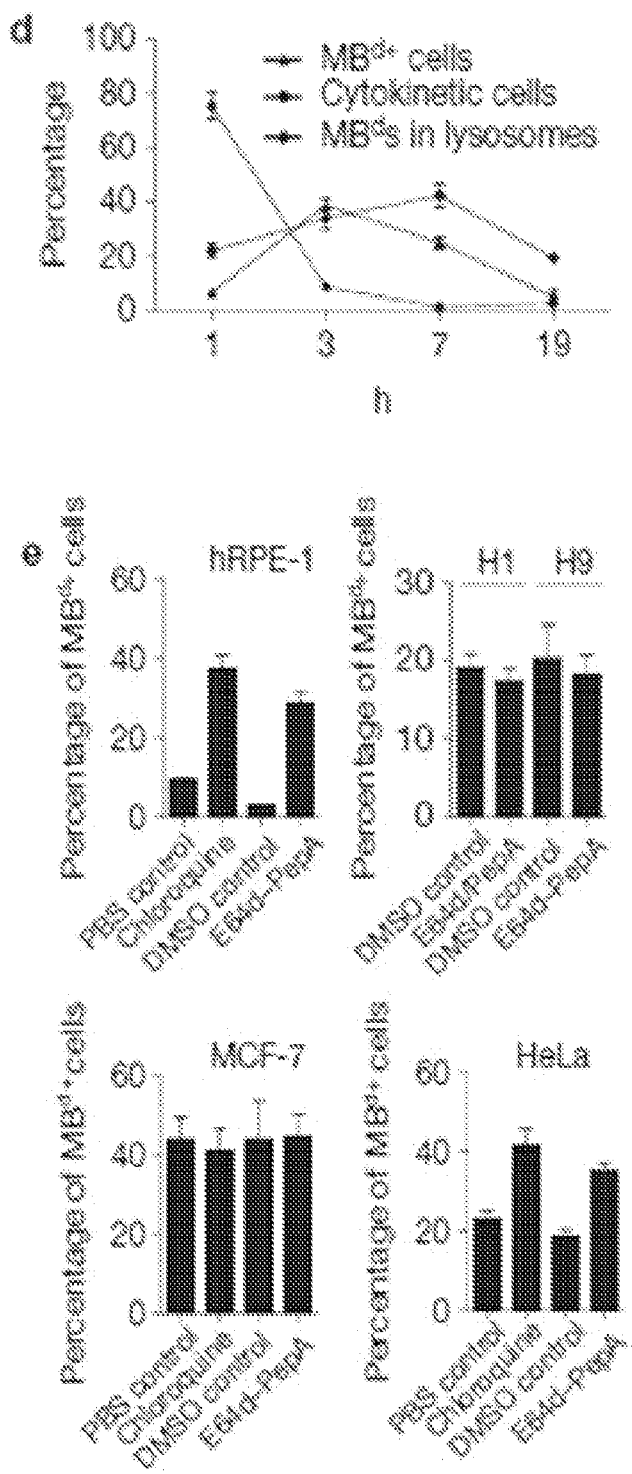

We next asked if MBds occupied different sites within MBd-rich and MBd-poor cells. To test this, we used the Fluorescence Protease Protection (FPP) assay (Lorenz et al., 2006, Nat. Methods, 3:205-210) to monitor degradation of MBds following plasma membrane permeabilization and protease addition (FIG. 5a). Under these conditions, MKLP1-GFP+ MBds were degraded in MBd-rich HeLa cells but not in MBd-poor hRPE-1 cells indicating that MBd-poor cells sequestered MBds in membrane-bound compartments whereas MBd-rich cells accumulated them in the cytoplasm (FIG. 5b). Importantly, the integrity of intracellular organelles was maintained during the course of these experiments.

Example 8

Stem Cells and Cancer Cells Evade Lysosomal Degradation of MBds

The protease resistance of MBds and low MBd-accumulation in MBd-poor hRPE-1 cells (FIGS. 4a and 5b) suggested that MBds were delivered to a membrane-bound compartment for degradation, such as the lysosome. Indeed, MBds were often found within LAMP2-labeled (Eskelinen et al., 2003, Trends Cell Biol., 13:137-145) lysosomes in MBd-poor cells (FIG. 5c). To test this further, we examined the fate of newly-formed MBds in synchronous populations of MBd-poor cells (FIG. 5d). Three hours after release from mitosis, the percent of MBd+ cells (MBd levels) peaked at ~40% (50% being the maximum since half the cells were 'born' without a MBd). This was followed by a peak in MBd localization to lysosomes (~42% at 7 hours; FIG. 5d) and then a decrease of MBds to baseline levels (16-19 hours; FIG. 5d). These data and the FPP data suggested that MBds in hRPE-1 cells entered the cytoplasm, moved into lysosomes and were degraded before the next cell cycle (FIG. 5b, d).

If lysosomes are involved in MBd degradation, lysosomal inhibition should increase MBd levels. Indeed, when lysosomal activity was inhibited in MBd-poor hRPE-1 cells with either chloroquine or E64d/PepA protease inhibitors (Klionsky et al., 2008, Autophagy, 4: 151-175) MBd levels (FIG. 5e) and the percent of MBds found within lysosomes (FIG. 5c) were elevated. In contrast, MBd levels and the percent of MBds in lysosomes in MBd-rich cells (hESC, MCF-7; FIG. 5c, e) were largely unaffected by lysosomal inhibition. The modest increase in MBd+HeLa cells (FIG. 5e) was consistent with their modest MBd-accumulating ability (FIG. 4a). We conclude that lysosomal degradation prevents MBd-accumulation in MBd-poor cells, but does not play a major role in MBd-rich cells (e.g. stem cells, CSCs) thus allowing MBds to accumulate.

Example 9

Autophagic Degradation Controls Intracellular MBd Levels

To determine how MBds were directed to lysosomes, we explored pathways leading to lysosomal degradation. Low autophagy levels in MCF-7 cells resulting from a deficiency in the autophagy gene, BECN1 (also known as Atg6) (Liang et al., 1999, Nature, 402:672-676), are consistent with high MBd-accumulation observed in this study (~26-fold over normal cells; FIG. 4a). High autophagy levels in DLD-1 cells (Sato et al., 2007, Cancer Res., 67:9677-84) are consistent with low MBd-accumulation observed in this study (only ~1.8-fold over normal cells; FIG. 4a). In agreement with this trend was the presence of MBds in autophagosomes of MBd-poor cells (FIG. 6a).

Figure 6:
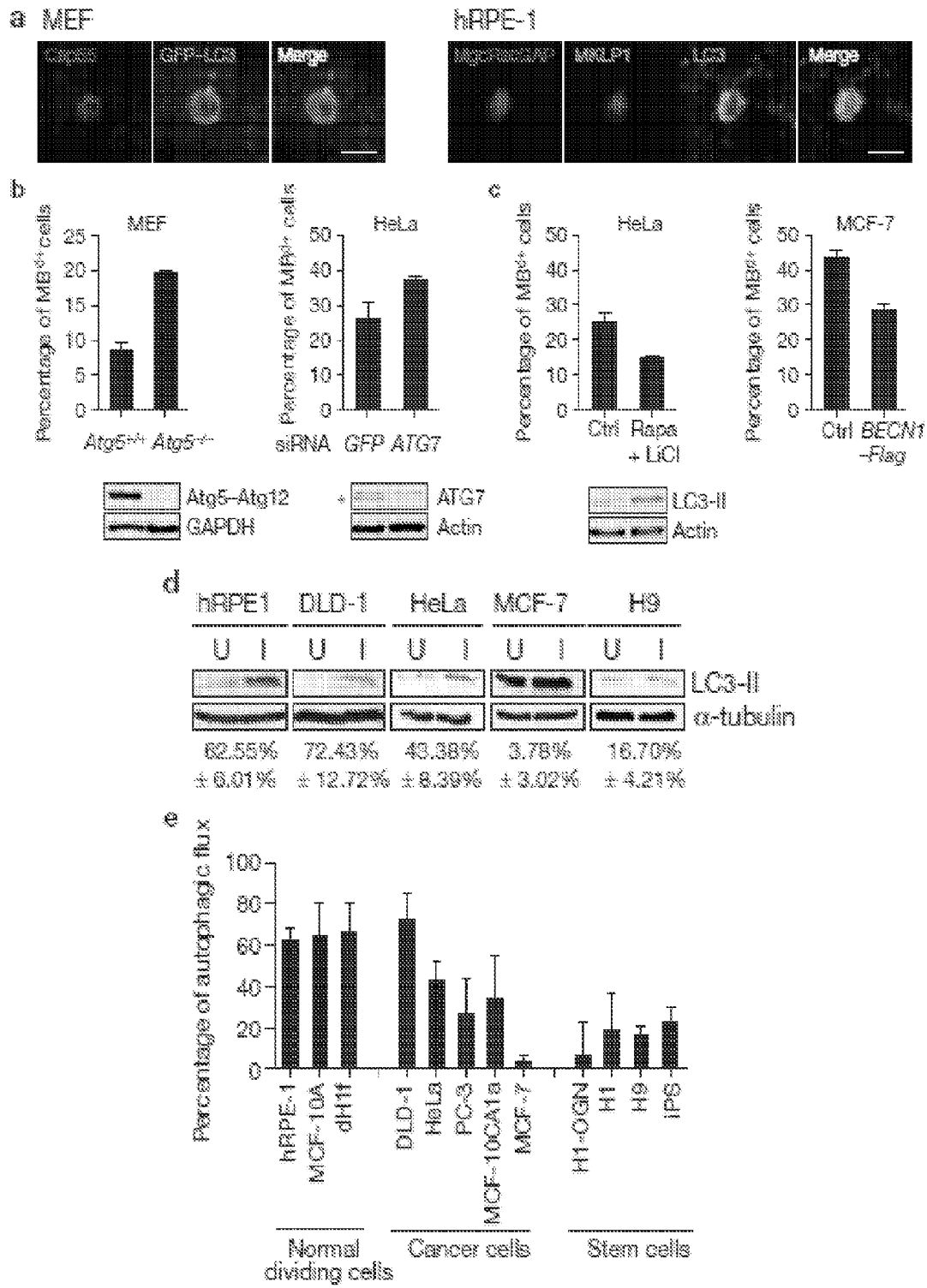
FIG. 6. Autophagy controls intracellular MBd levels. (a) Single-plane confocal images of MBds within LC3-positive autophagosomes in MEFs expressing GFP-LC3 (left) and in hRPE-1 cells stained for endogenous LC3 (right). MBd markers: Cep55, MKLP1, or mgcRACGAP. Autophagosomes: GFP-LC3 or LC3. Note that MKLP1 (blue) and mgcRAC-GAP (red) are co-localized (magenta) in the autophagosome (green), suggesting that MBds are sorted into autophagosomes. Bars, 2 μm. (b) Decreasing autophagy levels by deletion of Atg5 gene (left, MEFs) or depletion of Atg7 by siRNA (right, HeLa) significantly increases the percent of MBd+ cells (p=0.0019 and p=0.021, respectively, n=3). Immunoblots confirm loss of the Atg5-Atg12 conjugation in mutant cells and depletion of Atg7 (asterisk). (c) Rapamycin (Rapa) and lithium chloride (LiCl) co-treatment induces autophagy and decreases the percent of MBd+ cells (left, HeLa; p=0.0056, n=3). Immunoblots showing increased LC3-II levels confirm autophagy induction. Induction of autophagy by over-expression of Flag-tagged BECN1 reduces the percent of MBd+ cells (right, MCF-7; p=0.0008, n=4) (d) Representative immunoblots showing high autophagy levels in normal cells and low levels in stem cells and cancer cells. Autophagic flux (autophagic activity) was measured by changes in the levels of LC3-II, in the presence or absence of lysosomal inhibitors E64d/PepA. U, uninhibited. I, inhibited. Below, the average of the percent change in LC3-II levels after lysosomal inhibition from 3 experiments. α-tubulin, loading control. (e) Quantification of autophagic flux in different cell lines. Normal dividing cells (MBd-poor) typically have high autophagic flux, whereas stem and cancer cells (MBd-rich) have low autophagic flux. The data are presented as mean±s.d. (b-e).

Experimental reduction of autophagy activity using MEFs from Atg5-deleted mice (Kuma et al., 2004, Nature, 432:

1032-36) or by siRNA-mediated depletion of Atg7, increased MBd levels (FIG. 6b). Induction of autophagy by rapamycin and lithium chloride treatment (Sarkar et al., 2008, Hum. Mol. Genet., 17:170-178; Sarkar, 2005, J. Cell Biol., 170: 1101-11) in HeLa cells or by exogenous BECN1 expression in MCF-7 cells, decreased MBd levels (FIG. 6c). These results demonstrated the role of autophagy in regulating MBd levels in different cell types, and suggested an inverse relationship between autophagic activity and MBd-accumulation. This inverse relationship was revealed in 12 cell lines by LC3-II- (Klionsky et al., 2008, Autophagy, 4:151-175; Mizushima et al., 2007, Autophagy, 3:542-545) or p62- (Klionsky et al., 2008, Autophagy, 4:151-175; Bjorkoy et al., 2005, J. Cell Biol., 171:603-614; Komatsu et al., 2007, Cell, 131:1149-63) based measurements of autophagic activity (FIG. 6d, e). We conclude that MBd levels are, in part, modulated by cell type/lineage-specific autophagy (FIG. 3g-i, 4a, 6d and 6e).

Example 10

NBR1 Is an Autophagic Receptor for MBd-Specific Degradation

To test whether MBd degradation involves non-specific or receptor-mediated autophagy pathways (Mizushima et al., 2008, Nature, 451:1069-75)), we investigated the mammalian autophagic receptors, p62 (Bjorkoy et al., 2005, J. Cell Biol., 171:603-614; Komatsu et al., 2007, Cell, 131:1149-63; Pankiv et al., 2007, J. Biol. Chem., 282:24131-45) and NBR1 (Kirkin et al., 2009, Mol. Cell, 27:505-516; Waters et al., 2009, FEBS Lett., 583:1846-52). NBR1 and p62 localized to mitotic MBs and MBds (FIG. 7a, top), suggesting that MBd degradation involves receptor-mediated autophagy. NBR1 silencing in HeLa cells increased MBd levels to Atg7-silencing levels (FIGS. 6b and 7b), suggesting that NBR1 is likely a major autophagic receptor for MBd degradation. In contrast, p62 deletion (Komatsu et al., 2007, Cell, 131:1149-63) or siRNA-mediated p62 depletion had no detectable effect on MBd levels (FIG. 7b, c) or NBR1 recruitment to MBds (FIG. 7a, bottom).

To date, no MBd target(s) for autophagic degradation have been identified. Candidate-based screening revealed that endogenous NBR1 co-immunoprecipitated with the MB protein Cep55 in hRPE-1 cells (FIG. 7d). Cep55 over-expression increased MBd levels (FIG. 7e) and the level of NBR1-negative MBds (FIG. 7o, presumably through NBR1 sequestration in the cytoplasm (FIG. 7g). This suggested a role of Cep55 in NBR1-mediated MBd degradation. We propose that the Cep55/NBR1 interaction couples MBds to the autophagic machinery to control MBd fate.

Example 11

Cells Enriched in MBds Exhibit Increased Reprogramming Efficiency

We next examined the functional consequences of manipulating MBd levels. We first tested the role of MBds during reprogramming (Park et al., 2008, Nature, 451:141-146; Chan et al., 2009, Nat. Biotechnol., 27:1033-37; Zwaka et al., 203, Nat. Biotechnol., 21:319-321) in cells stably expressing NBR1-specific shRNAs (shNBR1) to increase MBd levels over controls (shNT). MBd levels increased ~1.8-fold in dH1f cells, ~1.5-fold in IMR90 (Yu et al., 2007, Science, 318:1917-20) embryonic fibroblasts, and ~1.9-fold in hHb2 (Park et al., 2008, Nature, 451:141-146) adult fibroblasts. Under these conditions, iPSC colony formation increased significantly in all three cell types depleted of NBR1: dH1f cells (up to 8.7-fold, avg. 3.1±0.5-fold), IMR90 cells (up to 4.2-fold, avg. 3.4±0.8-fold; FIG. 8a, b) and adult hFib2 cells (up to 2.5-fold, avg. 1.7±0.5-fold). Similar results were obtained with different batches of viruses, different combinations of reprogramming factors, and different viral delivery systems (see Methods). Importantly, increased reprogramming following NBR1-depletion occurred without significant changes in global autophagic activity (dH1f; FIG. 8c) or cell proliferation rate (shNBR1: 27.3±2.5 hrs; shNT: 26.8±4.5 hrs; n=6), suggesting that NBR1 is selective for MBd degradation.

Example 12

Cancer Cells Enriched in MBds Exhibit Increased in vitro Tumorigenicity

Because MBds selectively accumulate in stem cell niches, hESCs, and iPSCs, we reasoned that they may also accumulate in CSCs. On the basis of Hoechst 33343 extrusion, the side population (SP) of MCF-7 cells (Engelmann et al., 2008, Cancer Res., 68:2419-26) was isolated. These putative CSCs showed a 7-fold increase in MBd+ cells over the non-SP population (MP; FIG. 8d).

To directly address the role of MBds in cancer cells, MKLP1-GFP-expressing HeLa populations with high or low percentages of MBd+ cells were isolated by FACS, and tested for anchorage-independent growth. Increased colony formation was observed in the "MBd high" versus the "MBd low" population, and colony formation increased with increasing MBd levels (up to 4-fold; FIG. 8e). An increase in colony formation was also observed in MBd-enriched HeLa cells (FIG. 8f, left) and mouse hepatocarcinoma cells (134-4; FIG. 8f, right) following NBR1-silencing. Results of all three strategies suggest that MBds in cancer cell subpopulations may contribute to their tumorigenic potential.

Example 13

Materials and Methods

Cell Lines hESC and iPSC lines include H1 (WA01), H9 (WA09), H1-OGN (Oct4-EGFP knock-in H1) (Zwaka et al., 2003, Nat. Biotechnol., 21:319-321), and dH1f-iPS (Park et al., 2008, Nature, 451:141-146), which is reprogrammed from dH1f cells differentiated from H1-OGN (HSCI at Children's Hospital Boston). Differentiated lines include hRPE-1 (Clontech), MCF-10A, adult human fibroblasts (PCS-201-012, ATCC), hFib2 (Park et al., 2008, Nature, 451:141-146), IMR90 (CCL-186, ATCC), ex vivo C57BL/6 MEFs, GFP-LC3-expressing Atg5$^{-/-}$ and Atg5$^{+/+}$ MEFs[19], and p61$^{-/-}$ and p62$^{+/+}$ MEFs (Komatsu et al., 2007, Cell, 131:1149-63). Cancer cell lines include DLD-1, HeLa, NCC-IT, PC-3, U2OS, SAOS-2, 134-4, MCF-7, MCF-10AT, and MCF-10CA1a. Mouse skeletal muscle progenitors (SMPs) (Conboy et al., 2010, Meth. Mol. Biol., 621:165-173) and in vitro activated T cells were isolated and stimulated following standard protocols. Cells were used within 4 (primary cultures) or 10 (established cell lines, hESCs, and iPSCs) passages.

Immunofluorescence and Immunohistochemistry

Immunofluorescence was performed as described (Gromley et al., 2005, Cell, 123:75-87; Marzesco et al., 2005, J. Cell Sci., 118:2849-58; Xu et al., 2010, Mol. Cell Biol., 30:1329-40). To label lysosomes and autophagosomes, cells were permeabilized with 0.05% saponin in blocking buffer (10% goat serum/PBS). Preparations for immunohistochemistry were fixed with 4% paraformaldehyde/0.5% glutaraldehyde via perfusion. Testes were processed and stained following 2-4 hr post-fixation with 4% paraformaldehyde. MB-derived rings between spermatocyte syncytia (Greenbaum et al., 2007, Dev. Biol., 305:389-396) were observed if stained longer. Images were taken on a Zeiss Axioskop™ 2 microscope, a Zeiss Axiovert™ 200 microscope with PerkinElmer Ultra-View™ LAS spinning disc, or an Olympus BX-51™ microscope. Images were processed and analyzed with MetaMorph™ (Molecular Devices) and Imaris™ (Bitplane Inc.) software packages.

Electron Microscopy

Conventional EM: Mouse tissue, fixed with 5% glutaraldehyde in 50 mM sodium cacodylate buffer (pH=7.4) for 30 minutes via perfusion, was diced into 1-mm cubes for 1-hr post-fixation at 4° C. Cubes were washed with cacodylate buffer, stained and embedded in Spi-pon/Araldite, and sectioned at 70-500 nm before staining with 25% uranyl acetate and Reynold's lead citrate. Images were taken on a Philips CM12 electron microscope with an Erlangshen CCD Camera (Gatan).

Immunogold EM: MCF-7 cells on coverslips were preperm-eabilized for 60 seconds with preperm buffer (80 mM PIPES, pH6.8, 0.5 mM EGTA, 1 mM MgCl, 0.5% Triton X-100), fixed with 4% paraformaldehyde for 10 minutes, labeled for MKLP1 for 1 hour, processed as described (Mitchison et al., 1986, Cell, 45:515-527) using 12-nm gold-conjugated goat anti-rabbit IgG (Jackson ImmunoResearch) and embedded in Spi-pon/Araldite. 80-nm sections were cut, stained and viewed as above.

Time-Lapse Imaging

CETN1-GFP-expressing lines were grown on 35-mm MatTek dishes (MatTek Corp.) or coverslips before imaging (Gromley et al., 2005, Cell, 123:75-87). H9 hESCs were seeded on matrigel-coated dishes overnight, then transduced with CETN1-GFP, and grown for >72 hours in complete mTeSR1 medium (Stemcell Technologies). The transduced cells were imaged every 15 minutes in phenol red-free D-MEM/F12 medium (Invitrogen) with mTeSR1 supplement and 10 mM HEPES, and stained to confirm MBd inheritance. Duplicate dishes of transduced cells were stained for stem cell markers to ensure cell quality.

MBd Quantification

Quantification was based on the markers that: 1) labeled both mitotic MBs and MBds (MKLP1, mgcRACGAP, or Cep55); 2) labeled MBs differently than MBds (α-tubulin or Aurora B); 3) defined cell boundaries (α-tubulin or ZO-1). Because Cep55, MKLP1, and mgcRACGAP also label centrioles and spindle midzones, cells were co-stained with centrosome antibody (e.g. 5051), and a size threshold for MB/MBds (1 μm) was introduced to exclude non-MBd structures. Structures with MB-specific or non-MB/MBd labeling were excluded from MBd counts. Cell counts: For hESCs, 5-11 colonies were imaged from triplicates in each experiment. For other cell types, random fields were imaged until n>500 cells. Each dividing cell was considered one cell.

Doubling Time Calculations

Cells were seeded ($1-1.5 \times 10^5$/60-mm dish), and total cell counts were taken by hemocytometer every 24 hours for 4 days. Alternatively, cells were seeded ($2.5-5.0 \times 10^3$/well, 96-well plates), and the absorbance from an MTS-based colorimetric assay (#G3582; Promega Corp.) was used to estimate cell counts every 24 hours. Timepoints vs. $\text{Log}_{10}$(avg. cell counts or absorbance at that timepoint) was plotted and the slope ascertained. $T_{1/2}=\text{Log}_{10}(2)/\text{slope}$. For some cell lines, both methods were used and gave similar results.

MBd Localization Assays

Extracellular trypsin treatment: MKLP1-GFP-expressing HeLa cells grown in MatTek dishes were imaged every 3 minutes, and underwent no morphological changes upon replacement of media with PBS. After trypsin addition, GFP+ MBds were monitored for 60-90 minutes for intensity reduction (degradation) or detachment from cells (dissociation).

Co-culture assay: Equal numbers of monomeric RFP- or MKLP-GFP-expressing cells were seeded and co-cultured in 60-mm dishes with coverslips. Cells were stained 2 days later, and the percentage of GFP+ MBds associated with RFP+ cells was determined.

FPP assay: The FPP assay was carried out as reported (Lorenz et al., 2006, Nat. Methods, 3: 205-210) except cells were plated in MatTek dishes 24 hours before co-transfection of MKLP1-GFP and GAPDH-dsRed (Lipofectamine 2000, Invitrogen). Cells were permeabilized and then digested with proteinase K (50 μg ml$^{-1}$). Constructs labeling mitochondria, peroxisomes, ER and Golgi were used as controls.

Lysosome and Proteasome Assays

Cells at 70% confluency were incubated with chloroquine (200 μM/PBS; Sigma), E64d+ pepstatin A (E64d/PepA) (10 μg ml$^{-1}$/DMSO each; Sigma) (Klionsky et al., 2008, Autophagy, 4:151-175; Komatsu et al., 2007, Cell, 131:1149-63) or solvents alone (controls) for 22 hours before fixation. Lysosome inhibition was confirmed and visualized after 12-hour DQ-Red BSA (10 μg ml$^{-1}$; Invitrogen) incubation. Mitotic hRPE-1 cells were treated with proteasome inhibitors, MG132 (1 μM; Sigma) or lactacystin (50 μM; Sigma) 1 hour after replating.

Autophagy Manipulation Assays

MBds were quantified in >500 cells in triplicate unless otherwise noted.

Protein depletion: siRNAs targeting human Atg7 (Yu et al., 2004, Science, 304:1500-02), p62 (Pohl et al., 2009, Nat. Cell Biol., 11:65-70), NBR1 (Kirkin et al., 2009, Mol. Cell, 27:505-516) (2503-2521 bp, GenBank NM 005899), Lamin A/C (Gromley et al., 2005, Cell, 123:75-87), and GFP (5'-NNCAUGAAGCAGCACGACUUC-3'; SEQ ID NO:5) were Dharmacon. MBd levels were analyzed 48 hours after 1-nmol siRNA transfection (Oligofectamine, Invitrogen). For NBR1 and p62 experiments, only cells negative for p62 and/or NBR1 immunofluorescence were analyzed.

Beclin1 (BECN1) overexpression: MBd levels were analyzed in 265 Flag+ and 2200 control MCF-7 cells 48 hours after Flag-BECN1 (4 μg) or mock nucleofection (Amaxa).

LiCl+rapamycin treatment: MBd levels in HeLa cells were examined 24 hours after treatment with LiCl (10 mM; Sigma) and rapamycin (200 nM; Calbiochem), or with DMSO.

CEP55-EGFP Overexpression: MBd levels and its NBR1-association were assessed in hRPE-1 cells ($1 \times 10^5$/well, 6-well plates) 48 hours after CEP55-EGFP (1 μg), EGFP (1 μg) or mock transfection.

Biochemical Assays

Protease and phosphatase inhibitors, cell lysates, SDS-PAGE and immunoblotting were purchased or carried out as described (Gromley et al., 2005, Cell, 123:75-87) unless specified.

Autophagy flux determination: Lysates of E64d/PepA (I) and DMSO (U) treated cells were blotted for α-tubulin and LC3. LC3-II levels were determined and normalized to α-tubulin using ImageJ. Autophagic flux=|100−((U/I LC3-II level)×100)|.

Immunoprecipitation: hRPE-1 cell lysates (50 mM Tris-HCl pH 7.5, 150 mM NaCl, 2 mM EDTA, 1 mM EGTA, 1%

Triton X-100, 10% glycerol, 4° C.) were pre-cleared for 1 hour with protein G-plus conjugated agarose beads (Santa Cruz) at 4° C., incubated with 2 µg normal IgG, anti-Cep55 or anti-NBR1 antibodies for 3 hours at 4° C., and incubated overnight at 4° C. with 25 µl protein G-plus beads. Following washes with lysis buffer and elution, immunoprecipitated proteins were analyzed by SDS-PAGE and immunoblotting.

Assays for MBd Function

Cellular reprogramming: Viral production, transduction and reprogramming were performed as described (Park et al., 2008, 451:141-146; Chan et al., 2009, Nat. Biotechnol., 27:1033-37; Yu et al., 2007, Science, 318:1917-20; Loewer et al., 2010, Nat. Genet., 42:1113-17). Commercially-available shRNA against NBR1 (pSM2c-shNBR1, V2MM_36901; 4-22 bp, GenBank NM 005899) was cloned into pGIPZ lentiviral vector (Open Biosystems). Embryonic fibroblasts (IMR90), adult fibroblasts (hFib2) and dH1f cells were transduced with either NBR1-specific or non-targeting shRNA vector, and puromycin-selected to establish NBR1-depleted (shNBR1) and control (shNT) lines. dH1f ($2.5 \times 10^4$/assay) were reprogrammed with lentiviral vectors (Yu et al., 2009, Science, 324:797-801) (Addgene #21162 and 21164) expressing OCT4, SOX2, KLF4 and c-MYC (Park et al., 2008, 451:141-146; Chan et al., 2009, Nat. Biotechnol., 27:1033-37; Loewer et al., 2010, Nat. Genet., 42:1113-17), whereas the reprogramming of IMR90 and hFib2 cells ($5 \times 10^4$/assay) also included lentiviral vectors expressing Nanog and Lin28 (Yu et al., 2007, Science, 318:1917-20; Yu et al., 2009, Science, 324:797-801) (Addgene #21163). iPSC colonies were quantified on day 21 based on Tra-1-60 expression using ImageJ, as reported (Chan et al., 2009, Nat. Biotechnol., 27:1033-37; Loewer et al., 2010, Nat. Genet., 42:1113-17), and with parameters: >148 (threshold), 0.5-1 (circularity), and either 10-infinity or 30-infinity (size).

Side Population (SP) assay: The assays were carried out as previously described (Engelmann et al., 2008, Cancer Res., 68:2419-26) in MCF-7 cells. The MBd levels in SP and non-SP populations were determined as described above.

Soft-agar assays: "MBd high" and "MBd low" subpopulations of MKLP1-GFP-expressing HeLa cells were separated by FACS, and plated in soft-agar ($2.5 \times 10^4$/well, 6-well plates). The MBd levels were determined 12-15 hours after plating aliquots of subpopulations onto coverslips. For the NBR1-silencing soft-agar assay, NBR1-depleted (shNBR1) and control (shNT) cells ($1 \times 10^5$/100-mm dish) were plated. For both assays, cells were grown for ~3 weeks at 37° C., and stained as described (Sachdev et al., 2009, BMC Cancer, 12:9-12). Colonies were quantified microscopically, and the average from triplicate wells or plates presented.

Antibodies

Antibodies to the Following Proteins/Tags were Used in this Study:

Atg5 (1:2000, Cosmo Bio, CAC-TMD-PH-ATG); Atg7 (1:1000, ProSci, 3617); Actin (1:300, Sigma, AC-40); Aurora B (1:100, BD Trans Lab, 611082); CD13 (1:50, BioLegend, 301707); CD133 (1:200, eBioscience, 14-1331); Cep55 (1:50, 1:100 and 1:1000 for immunofluorescence, Abnova #H00055165-B01, Abnova #H00055165-A01, and the gift from K. Kurtche, respectively; 1:500 for immunoblotting, Genetax #GTX112190); hCenexin1 (1:100); Centriolin (1:200, ref. 9); Flag (1:200, Sigma, F7425); GAPDH (1:8000; Santa Cruz, S.C.-32233); GFP (1:1000; Abcam, ab6556 and Santa Cruz, sc-9996); GT335 (1:100; a gift from P. Denoulet); β1-Integrin (1:50; BD Phramingen); K15 (1:100; Lab Vision, MS-1068-P); LC3 (1:10 for immunofluorescence, Nano Tools, LC3-5F10; 1:300 for immunoblotting, Novus Bio NB100-2331); LAMP2 (1:50, H4B4 from DSHB); mgcRACGAP (1:500, Abcam, ab2270); MKLP1 (1:1000 for immunofluorescence, 1:200 for immunohistochemistry, 1:10 for immuno-EM, Santa Cruz, sc-867); NBR1 (1:500, Abnova, H00004077-B01P); p62, human samples (1:500, BD Trans Lab, 610833); p62, mouse samples (1:1000, Progen, GP62-C); RFP (1:200, Clontech, 632496); Na-K-AT-Pase (1:15, α6F from DSHB); α-tubulin (1:100 for immunofluorescence, 1:400 for immunoblotting, Sigma, T9026a; 1:100 for immunofluorescence, Millipore, CBL270); α-tubulin-FITC (1:300, Sigma, F2168); Tra-1-60-biotin (1:200, eBioscience, 13-8863); Ubiquitin (1:2000, BD BioSci, #550944); WGA-Alexa Fluor 555 (1:200, Molecular Probes, W32464); ZO-1-FITC (1:50, Zymed, 33-9111).

Statistics

Data was analyzed by Student's one-tailed paired t-test or unpaired with Welch's correction unless specified. One-way ANOVA was used in conjunction with Tukey's test for comparisons among multiple groups. For the EdU-labeling assay, the EdU intensity was first logarithmically transformed for the use of one-way ANOVA. Statistically analyzed experiments were completed at least 3 times.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of inducing degradation of a midbody derivative in a cancer cell, the method comprising:
   (a) introducing into the cancer cell a nucleic acid that comprises a sequence encoding a Neighbor of BRCA1 (NBR1) polypeptide, a composition comprising an NBR1 polypeptide, or an artificial transcription factor that increases transcription of an NBR1 gene,
   thereby increasing the amount of NBR1 polypeptide in the cancer cell and inducing degradation of a midbody derivative in the cancer cell.

2. The method of claim 1, wherein the method comprises introducing into the cancer cell a nucleic acid that comprises a sequence encoding an NBR1 polypeptide.

3. The method of claim 1, wherein the method comprises introducing into the cancer cell a composition comprising an NBR1 polypeptide or an artificial transcription factor that increases transcription of an NBR1 gene.

4. The method of claim 3, wherein the composition comprises the NBR1 polypeptide or artificial transcription factor fused with a cell-penetrating peptide, or comprises a liposome.

5. The method of claim 1, wherein the cancer cell is a cancer stem cell.

6. The method of claim 1, wherein the cancer cell is in a subject.

7. A method of treating cancer in a subject, the method comprising:
   (a) introducing into a cancer cell in the subject a nucleic acid that comprises a sequence encoding a Neighbor of BRCA1 (NBR1) polypeptide, a composition comprising an NBR1 polypeptide, or an artificial transcription factor that increases transcription of an NBR1 gene,
   thereby increasing the amount of NBR1 polypeptide and midbody derivative degradation in cancer cells and treating cancer in the subject.

8. The method of claim 7, wherein the method comprises introducing into the cancer cell a nucleic acid that comprises a sequence encoding an NBR1 polypeptide.

9. The method of claim 7, wherein the method comprises introducing into the cancer cell a composition comprising an NBR1 polypeptide or an artificial transcription factor that increases transcription of a NBR1 gene.

10. The method of claim 9, wherein the composition comprises the NBR1 polypeptide or artificial transcription factor fused with a cell-penetrating peptide, or comprises a liposome.

11. The method of claim 7, wherein the cancer is a breast cancer.

12. The method of claim 7, wherein the subject is a human.

13. The method of claim 1, wherein the nucleic acid is a vector.

14. The method of claim 13, wherein the vector is a viral vector.

15. The method of claim 1, wherein the cancer cell is a hepatic cancer cell or an adenocarcinoma cancer cell.

16. The method of claim 7, wherein the nucleic acid is a vector.

17. The method of claim 16, wherein the vector is a viral vector.

18. The method of claim 7, wherein the cancer cell is a cancer stem cell.

19. The method of claim 7, wherein the cancer is hepatic cancer and the cancer cells are hepatic cancer cells.

20. The method of claim 7, wherein the cancer is an adenocarcinoma and the cancer cells are adenocarcinoma cancer cells.

* * * * *

SEQUENCE LISTING

<160> NUMBER OF SEQ ID NOS: 5

<210> SEQ ID NO 1
<211> LENGTH: 464
<212> TYPE: PRT
<213> ORGANISM: Homo sapiens

<400> SEQUENCE: 1

Met Ser Ser Arg Ser Thr Lys Asp Leu Ile Lys Ser Lys Trp Gly Ser
1               5                   10                  15

Lys Pro Ser Asn Ser Lys Ser Glu Thr Thr Leu Glu Lys Leu Lys Gly
            20                  25                  30

Glu Ile Ala His Leu Lys Thr Ser Val Asp Glu Ile Thr Ser Gly Lys
        35                  40                  45

```
Gly Lys Leu Thr Asp Lys Glu Arg His Arg Leu Leu Glu Lys Ile Arg
 50                  55                  60
Val Leu Glu Ala Glu Lys Lys Asn Ala Tyr Gln Leu Thr Glu Lys
 65                  70                  75                  80
Asp Lys Glu Ile Gln Arg Leu Arg Asp Gln Leu Lys Ala Arg Tyr Ser
                     85                  90                  95
Thr Thr Ala Leu Leu Glu Gln Leu Glu Thr Thr Arg Glu Gly Glu
                100                 105                 110
Arg Arg Glu Gln Val Leu Lys Ala Leu Ser Glu Glu Lys Asp Val Leu
            115                 120                 125
Lys Gln Gln Leu Ser Ala Ala Thr Ser Arg Ile Ala Glu Leu Glu Ser
 130                 135                 140
Lys Thr Asn Thr Leu Arg Leu Ser Gln Thr Val Ala Pro Asn Cys Phe
 145                 150                 155                 160
Asn Ser Ser Ile Asn Asn Ile His Glu Met Glu Ile Gln Leu Lys Asp
                165                 170                 175
Ala Leu Glu Lys Asn Gln Gln Trp Leu Val Tyr Asp Gln Gln Arg Glu
                180                 185                 190
Val Tyr Val Lys Gly Leu Leu Ala Lys Ile Phe Glu Leu Glu Lys Lys
            195                 200                 205
Thr Glu Thr Ala Ala His Ser Leu Pro Gln Gln Thr Lys Lys Pro Glu
 210                 215                 220
Ser Glu Gly Tyr Leu Gln Glu Lys Gln Lys Cys Tyr Asn Asp Leu
 225                 230                 235                 240
Leu Ala Ser Ala Lys Lys Asp Leu Glu Val Glu Arg Gln Thr Ile Thr
                245                 250                 255
Gln Leu Ser Phe Glu Leu Ser Glu Phe Arg Arg Lys Tyr Glu Glu Thr
                260                 265                 270
Gln Lys Glu Val His Asn Leu Asn Gln Leu Leu Tyr Ser Gln Arg Arg
            275                 280                 285
Ala Asp Val Gln His Leu Glu Asp Asp Arg His Lys Thr Glu Lys Ile
 290                 295                 300
Gln Lys Leu Arg Glu Glu Asn Asp Ile Ala Arg Gly Lys Leu Glu Glu
 305                 310                 315                 320
Glu Lys Lys Arg Ser Glu Glu Leu Leu Ser Gln Val Gln Phe Leu Tyr
                325                 330                 335
Thr Ser Leu Leu Lys Gln Gln Glu Glu Gln Thr Arg Val Ala Leu Leu
                340                 345                 350
Glu Gln Gln Met Gln Ala Cys Thr Leu Asp Phe Glu Asn Glu Lys Leu
            355                 360                 365
Asp Arg Gln His Val His Gln Leu His Val Ile Leu Lys Glu Leu
 370                 375                 380
Arg Lys Ala Arg Asn Gln Ile Thr Gln Leu Glu Ser Leu Lys Gln Leu
 385                 390                 395                 400
His Glu Phe Ala Ile Thr Glu Pro Leu Val Thr Phe Gln Gly Glu Thr
                405                 410                 415
Glu Asn Arg Glu Lys Val Ala Ala Ser Pro Lys Ser Pro Thr Ala Ala
            420                 425                 430
Leu Asn Glu Ser Leu Val Glu Cys Pro Lys Cys Asn Ile Gln Tyr Pro
            435                 440                 445
Ala Thr Glu His Arg Asp Leu Leu Val His Val Glu Tyr Cys Ser Lys
 450                 455                 460
```

<210> SEQ ID NO 2
<211> LENGTH: 2637
<212> TYPE: DNA
<213> ORGANISM: Homo sapiens

<400> SEQUENCE: 2

| | | | | | |
|---|---|---|---|---|---|
| cacacctgat | ggtgtgactc | ggccgacgcg | agcgccgcgc | ttcgcttcag | ctgctagctg | 60 |
| gcccaaggga | ggcgaccgcg | gagggtggcg | aggggcggcc | aggacccgca | gccccggggc | 120 |
| cgggccggtc | cggaccgcca | gggagggcag | gtcagtgggc | agatcgcgtc | cgcgggattc | 180 |
| aatctctgcc | cgctctgata | acagtccttt | tccctggcgc | tcacttcgtg | cctggcaccc | 240 |
| ggctgggcgc | ctcaagaccg | ttgtctcttc | gatcgcttct | ttggacttgg | cgaccatttc | 300 |
| agagatgtct | tccagaagta | ccaaagattt | aattaaaagt | aagtggggat | cgaagcctag | 360 |
| taactccaaa | tccgaaacta | cattagaaaa | attaaaggga | gaaattgcac | acttaaagac | 420 |
| atcagtggat | gaaatcacaa | gtgggaaagg | aaagctgact | gataaagaga | gacacagact | 480 |
| tttggagaaa | attcgagtcc | ttgaggctga | gaaggagaag | aatgcttatc | aactcacaga | 540 |
| gaaggacaaa | gaaatacagc | gactgagaga | ccaactgaag | gccagatata | gtactaccgc | 600 |
| attgcttgaa | cagctggaag | agacaacgag | agaaggagaa | aggagggagc | aggtgttgaa | 660 |
| agccttatct | gaagagaaag | acgtattgaa | acaacagttg | tctgctgcaa | cctcacgaat | 720 |
| tgctgaactt | gaaagcaaaa | ccaatacact | ccgtttatca | cagactgtgg | ctccaaactg | 780 |
| cttcaactca | tcaataaata | atattcatga | aatggaaata | cagctgaaag | atgctctgga | 840 |
| gaaaaatcag | cagtggctcg | tgtatgatca | gcagcgggaa | gtctatgtaa | aaggacttt | 900 |
| agcaaagatc | tttgagttgg | aaaagaaaac | ggaaacagct | gctcattcac | tcccacagca | 960 |
| gacaaaaaag | cctgaatcag | aaggttatct | tcaagaagag | aagcagaaat | gttacaacga | 1020 |
| tctcttggca | agtgcaaaaa | aagatcttga | ggttgaacga | caaaccataa | ctcagctgag | 1080 |
| ttttgaactg | agtgaatttc | gaagaaaata | tgaagaaacc | caaaagaag | ttcacaattt | 1140 |
| aaatcagctg | ttgtattcac | aaagaagggc | agatgtgcaa | catctggaag | atgataggca | 1200 |
| taaaacagag | aagatacaaa | aactcaggga | agagaatgat | attgctaggg | gaaaacttga | 1260 |
| agaagagaag | aagagatccg | aagagctctt | atctcaggtc | cagtttctt | acacatctct | 1320 |
| gctaaagcag | caagaagaac | aaacaagggt | agctctgttg | gaacaacaga | tgcaggcatg | 1380 |
| tactttagac | tttgaaaatg | aaaaactcga | ccgtcaacat | gtgcagcatc | aattgcatgt | 1440 |
| aattcttaag | gagctccgaa | aagcaagaaa | tcaaataaca | cagttggaat | ccttgaaaca | 1500 |
| gcttcatgag | tttgccatca | cagagccatt | agtcactttc | caaggagaga | ctgaaaacag | 1560 |
| agaaaaagtt | gccgcctcac | caaaaagtcc | cactgctgca | ctcaatgaaa | gcctggtgga | 1620 |
| atgtcccaag | tgcaatatac | agtatccagc | cactgagcat | cgcgatctgc | ttgtccatgt | 1680 |
| ggaatactgt | tcaaagtagc | aaaataagta | tttgttttga | tattaaaaga | ttcaatactg | 1740 |
| tattttctgt | tagcttgtgg | gcattttgaa | ttatatattt | cacattttgc | ataaaactgc | 1800 |
| ctatctacct | ttgacactcc | agcatgctag | tgaatcatgt | atcttttagg | ctgctgtgca | 1860 |
| tttctcttgg | cagtgatacc | tccctgacat | ggttcatcat | caggctgcaa | tgacagaatg | 1920 |
| tggtgagcag | cgtctactga | gactactaac | attttgcact | gtcaaaatac | ttggtgagga | 1980 |
| aaagatagct | caggttattg | ctaatgggtt | aatgcaccag | caagcaaaat | attttatgtt | 2040 |
| ttgggggttt | tgaaaaatca | agataattaa | accaaggatc | ttaactgtgt | tcgcattttt | 2100 |
| tatccaagca | cttagaaaac | ctacaatcct | aattttgatg | tccattgtta | agaggtggtg | 2160 |

```
atagatacta ttttttttt catattgtat agcggttatt agaaaagttg gggattttct    2220
tgatctttat tgctgcttac cattgaaact taacccagct gtgttcccca actctgttct    2280
gcgcacgaaa cagtatctgt ttgaggcata atcttaagtg ccacacaca atgttttctc    2340 ttatgttatc tggcagtaac tgtaacttga attacattag cacattctgc ttagctaaaa    2400
ttgttaaaat aaactttaat aaacccatgt agccctctca tttgattgac agtattttag    2460
ttatttttgg cattcttaaa gctgggcaat gtaatgatca gatctttgtt tgtctgaaca    2520 ggtatttta tacatgcttt ttgtaaacca aaaacttta aatttcttca ggttttctaa       2580
catgcttacc actgggctac tgtaaatgag aaaagaataa aattatttaa tgtttta        2637
```

<210> SEQ ID NO 3
<211> LENGTH: 966
<212> TYPE: PRT
<213> ORGANISM: Homo sapiens

<400> SEQUENCE: 3

```
Met Glu Pro Gln Val Thr Leu Asn Val Thr Phe Lys Asn Glu Ile Gln
 1               5                  10                  15

Ser Phe Leu Val Ser Asp Pro Glu Asn Thr Thr Trp Ala Asp Ile Glu
            20                  25                  30

Ala Met Val Lys Val Ser Phe Asp Leu Asn Thr Ile Gln Ile Lys Tyr
        35                  40                  45

Leu Asp Glu Glu Asn Glu Glu Val Ser Ile Asn Ser Gln Gly Glu Tyr
    50                  55                  60

Glu Glu Ala Leu Lys Met Ala Val Lys Gln Gly Asn Gln Leu Gln Met
65                  70                  75                  80

Gln Val His Glu Gly His His Val Asp Glu Ala Pro Pro Val
                85                  90                  95

Val Gly Ala Lys Arg Leu Ala Ala Arg Ala Gly Lys Lys Pro Leu Ala
            100                 105                 110

His Tyr Ser Ser Leu Val Arg Val Leu Gly Ser Asp Met Lys Thr Pro
        115                 120                 125

Glu Asp Pro Ala Val Gln Ser Phe Pro Leu Val Pro Cys Asp Thr Asp
    130                 135                 140

Gln Pro Gln Asp Lys Pro Pro Asp Trp Phe Thr Ser Tyr Leu Glu Thr
145                 150                 155                 160

Phe Arg Glu Gln Val Val Asn Glu Thr Val Glu Lys Leu Glu Gln Lys
                165                 170                 175

Leu His Glu Lys Leu Val Leu Gln Asn Pro Ser Leu Gly Ser Cys Pro
            180                 185                 190

Ser Glu Val Ser Met Pro Thr Ser Glu Glu Thr Leu Phe Leu Pro Glu
        195                 200                 205

Asn Gln Phe Ser Trp His Ile Ala Cys Asn Asn Cys Gln Arg Arg Ile
    210                 215                 220

Val Gly Val Arg Tyr Gln Cys Ser Leu Cys Pro Ser Tyr Asn Ile Cys
225                 230                 235                 240

Glu Asp Cys Glu Ala Gly Pro Tyr Gly His Asp Thr Asn His Val Leu
                245                 250                 255

Leu Lys Leu Arg Arg Pro Val Val Gly Ser Ser Glu Pro Phe Cys His
            260                 265                 270

Ser Lys Tyr Ser Thr Pro Arg Leu Pro Ala Ala Leu Glu Gln Val Arg
        275                 280                 285
```

-continued

```
Leu Gln Lys Gln Val Asp Lys Asn Phe Leu Lys Ala Glu Lys Gln Arg
290                 295                 300
Leu Arg Ala Glu Lys Lys Gln Arg Lys Ala Glu Val Lys Glu Leu Lys
305                 310                 315                 320
Lys Gln Leu Lys Leu His Arg Lys Ile His Leu Trp Asn Ser Ile His
            325                 330                 335
Gly Leu Gln Ser Pro Lys Ser Pro Leu Gly Arg Pro Glu Ser Leu Leu
            340                 345                 350
Gln Ser Asn Thr Leu Met Leu Pro Leu Gln Pro Cys Thr Ser Val Met
        355                 360                 365
Pro Met Leu Ser Ala Ala Phe Val Asp Glu Asn Leu Pro Asp Gly Thr
370                 375                 380
His Leu Gln Pro Gly Thr Lys Phe Ile Lys His Trp Arg Met Lys Asn
385                 390                 395                 400
Thr Gly Asn Val Lys Trp Ser Ala Asp Thr Lys Leu Lys Phe Met Trp
            405                 410                 415
Gly Asn Leu Thr Leu Ala Ser Thr Glu Lys Lys Asp Val Leu Val Pro
            420                 425                 430
Cys Leu Lys Ala Gly His Val Gly Val Val Ser Val Glu Phe Ile Ala
        435                 440                 445
Pro Ala Leu Glu Gly Thr Tyr Thr Ser His Trp Arg Leu Ser His Lys
450                 455                 460
Gly Gln Gln Phe Gly Pro Arg Val Trp Cys Ser Ile Ile Val Asp Pro
465                 470                 475                 480
Phe Pro Ser Glu Glu Ser Pro Asp Asn Ile Glu Lys Gly Met Ile Ser
            485                 490                 495
Ser Ser Lys Thr Asp Asp Leu Thr Cys Gln Gln Glu Glu Thr Phe Leu
            500                 505                 510
Leu Ala Lys Glu Glu Arg Gln Leu Gly Glu Val Thr Glu Gln Thr Glu
        515                 520                 525
Gly Thr Ala Ala Cys Ile Pro Gln Lys Ala Lys Asn Val Ala Ser Glu
530                 535                 540
Arg Glu Leu Tyr Ile Pro Ser Val Asp Leu Leu Thr Ala Gln Asp Leu
545                 550                 555                 560
Leu Ser Phe Glu Leu Leu Asp Ile Asn Ile Val Gln Glu Leu Glu Arg
            565                 570                 575
Val Pro His Asn Thr Pro Val Asp Val Thr Pro Cys Met Ser Pro Leu
            580                 585                 590
Pro His Asp Ser Pro Leu Ile Glu Lys Pro Gly Leu Gly Gln Ile Glu
        595                 600                 605
Glu Glu Asn Glu Gly Ala Gly Phe Lys Ala Leu Pro Asp Ser Met Val
610                 615                 620
Ser Val Lys Arg Lys Ala Glu Asn Ile Ala Ser Val Glu Glu Ala Glu
625                 630                 635                 640
Glu Asp Leu Ser Gly Thr Gln Phe Val Cys Glu Thr Val Ile Arg Ser
            645                 650                 655
Leu Thr Leu Asp Ala Ala Pro Asp His Asn Pro Pro Cys Arg Gln Lys
            660                 665                 670
Ser Leu Gln Met Thr Phe Ala Leu Pro Glu Gly Pro Leu Gly Asn Glu
        675                 680                 685
Lys Glu Glu Ile Ile His Ile Ala Glu Glu Ala Val Met Glu Glu
690                 695                 700
Glu Glu Asp Glu Glu Asp Glu Glu Glu Glu Asp Glu Leu Lys Asp Glu
```

```
                    705                 710                 715                 720
            Val Gln Ser Gln Ser Ala Ser Ser Glu Asp Tyr Ile Ile Ile Leu
                            725                 730                 735
            Pro Glu Cys Phe Asp Thr Ser Arg Pro Leu Gly Asp Ser Met Tyr Ser
                        740                 745                 750
            Ser Ala Leu Ser Gln Pro Gly Leu Glu Arg Gly Ala Glu Gly Lys Pro
                        755                 760                 765
            Gly Val Glu Ala Gly Gln Glu Pro Ala Glu Ala Gly Glu Arg Leu Pro
                770                 775                 780
            Gly Gly Glu Asn Gln Pro Gln Glu His Ser Ile Ser Asp Ile Leu Thr
            785                 790                 795                 800
            Thr Ser Gln Thr Leu Glu Thr Val Pro Leu Ile Pro Glu Val Val Glu
                            805                 810                 815
            Leu Pro Pro Ser Leu Pro Arg Ser Pro Cys Val His His His Gly
                        820                 825                 830
            Ser Pro Gly Val Asp Leu Pro Val Thr Ile Pro Glu Val Ser Ser Val
                        835                 840                 845
            Pro Asp Gln Ile Arg Gly Glu Pro Arg Gly Ser Ser Gly Leu Val Asn
                850                 855                 860
            Ser Arg Gln Lys Ser Tyr Asp His Ser Arg His His His Gly Ser Ser
            865                 870                 875                 880
            Ile Ala Gly Gly Leu Val Lys Gly Ala Leu Ser Val Ala Ala Ser Ala
                            885                 890                 895
            Tyr Lys Ala Leu Phe Ala Gly Pro Pro Val Thr Ala Gln Pro Ile Ile
                        900                 905                 910
            Ser Glu Asp Gln Thr Ala Ala Leu Met Ala His Leu Phe Glu Met Gly
                        915                 920                 925
            Phe Cys Asp Arg Gln Leu Asn Leu Arg Leu Leu Lys Lys His Asn Tyr
                        930                 935                 940
            Asn Ile Leu Gln Val Val Thr Glu Leu Leu Gln Leu Asn Asn Asn Asp
            945                 950                 955                 960
            Trp Tyr Ser Gln Arg Tyr
                            965

<210> SEQ ID NO 4
<211> LENGTH: 4598
<212> TYPE: DNA
<213> ORGANISM: Homo sapiens

<400> SEQUENCE: 4
ggatagcggc agagccggta gcggacggtc cttgcattgg cctccggcag gcgcccccg      60 ggggcgggaa gctgcctcac agcatggaac cacaggttac tctaaatgtg acttttaaaa    120
atgaaattca aagctttctg gtttctgatc agaaaatac aacttgggct gatatcgaag    180
ctatggtaaa agtttcattt gatctgaata ctattcaaat aaaatacctg gatgaggaaa    240
atgaagaggt atccatcaac agtcaaggag aatatgaaga agcgcttaag atggcagtta    300
aacagggaaa ccaactgcag atgcaagtcc acgaaggca ccatgtcgtt gatgaagccc      360 caccccagt tgtaggagca aaacgactag ctgccagggc agggagaag ccacttgcac        420 attactcttc actggtgaga gtcttgggat cagacatgaa gaccccagag gatcctgcag     480
tgcagtcgtt tccacttgtt ccatgtgaca cagaccagcc tcaagacaag cccccagact    540
ggttcacaag ctacctggag acgttcagag aacaagtggt taacgaaacg gttgagaagc    600
ttgaacagaa attacatgaa aagcttgtcc tccagaaccc atccttgggt tcttgtccct    660
```

```
cagaagtctc aatgcctact tcagaagaaa cattgttttt gccagaaaac cagttcagct    720
ggcatattgc ttgcaacaac tgccaaagaa ggattgttgg tgtccgctac cagtgtagcc    780
tatgcccatc ctacaatatc tgtgaagatt gtgaagcagg ccatatggc catgacacta     840 accacgtcct gctgaagttg cggagacctg ttgtgggctc ctctgaaccg ttctgtcact    900
caaagtactc tactcctcgt cttcctgctg ctctggaaca agtcaggctc cagaaacagg    960
ttgataagaa cttttcttaaa gcagaaaagc aaaggttgcg agctgagaag aaacaacgta   1020
aagcagaggt caaggaactt aaaaagcagc ttaaactcca taggaaaatt cacctgtgga   1080
attcaatcca tggactccag agccccaagt ctcctttagg ccgacctgag agcttgctcc   1140
agtctaatac cctgatgctc cctttgcagc cctgtacctc cgttatgcca atgctcagtg   1200
cagcatttgt ggatgagaat ttgcctgatg ggactcacct tcagccagga accaagttta   1260
tcaaacactg gaggatgaaa aatacaggaa atgtaaagtg gagtgcagac acaaagctca   1320
agttcatgtg gggaaacctg actttggctt ccacagaaaa gaaggatgtt ttggttccct   1380
gcctcaaggc cggccatgtg ggagttgtat ctgtggagtt cattgcccca gccttggagg   1440
gaacgtatac ttcccattgg cgtctttctc acaaaggcca gcaatttggg cctcgggtct   1500
ggtgcagtat catagtagat cctttcccct ccgaagagag ccctgataac attgaaaagg   1560
gcatgatcag ctcaagcaaa actgatgatc tcacctgcca gcaagaggaa acttttcttc   1620
tggctaaaga agaaagacag cttggtgaag tgactgagca gacagaaggg acagcagcct   1680
gcatcccaca gaaggcaaaa aatgttgcca gtgagaggga gctctacatc ccatctgtgg   1740
atcttctgac tgcccaggac ctgctgtcct ttgagctgtt ggatataaac attgttcaag   1800
agttggagag agtgccccac aacacccctg tggatgtgac tccctgcatg tctcctctgc   1860
cacatgacag tcctttaata gagaagccag gcttggggca gatagaggaa gagaatgaag   1920
gggcaggatt taaagcactt cctgattcta tggtgtcagt aaagaggaag gctgagaaca   1980
ttgcttctgt ggaggaagca gaagaagacc tgagtgggac ccagtttgtg tgtgagacag   2040
taatccgatc ccttaccttg gatgctgccc cagaccacaa ccctccttgc agacagaagt   2100
ccttgcagat gacatttgcc ttgcctgaag gaccacttgg aaatgagaag gaggagatta   2160
tccatatcgc tgaggaagaa gctgtcatgg aggaggagga ggatgaggag gatgaggagg   2220
aggaggatga gctcaaagat gaagttcaaa gtcagtcctc tgcttcctca gaggattaca   2280
tcatcatcct gcctgagtgc tttgatacca gccgccccct gggggattct atgtacagct   2340
ctgcgctctc acagccaggc ctggagcgag gtgctgaagg caagcctggg gttgaggctg   2400 gcaggaacc agctgaggct ggggaaagac tccctggagg ggagaaccag ccacaggagc   2460
acagcataag tgacatcctc acgacctcac agactctgga acagtgccc ctaatcccag   2520 aggtagtgga gcttccaccg tcactgccca ggagctctcc ttgtgtacat catcatggtt   2580
ccccaggagt ggatttacca gttaccatac cagaagtttc ttcagtccct gatcagatca   2640
gaggagagcc cagaggctca tcaggacttg taaacagcag acagaagagc tatgaccact   2700
caaggcacca tcatgggagc agcattgctg gaggactggt gaagggggct ttgtctgttg   2760
ctgcctctgc atacaaggcc ctgtttgctg gccaccagt cactgcacag ccaataattt   2820
ctgaagatca gacagcagcc ctgatggccc atctctttga aatgggattc tgtgacaggc   2880
agctgaacct acggctgctg aagaaacaca attacaatat cctgcaggtt gtgacagaac   2940
ttcttcagtt aaacaacaac gactggtaca gccaacgcta ttgaggagtg accttgtatt   3000
```

```
aaataactgc ctgctgctca gagatgatct ttattctgtc attggggtat gggatagaag    3060
cccttgctta tttttaatct gatgaatctg tatagagccc atcgttgagt taccaagaca    3120
atacctgcta cagtattttg gggagcaaac taaagaccag aacttaaatt ttcactttag    3180
acattggatg aatagtatga agacagtttt tcagttgatt tggataaaac tatttagtg    3240 cattgacaag tgtaacttca acttcatata gaaccatttt tctttctgct tttattgaaa    3300
ctgagtattt ttctttggct aatgtggatt ttttatgggg atatctgtta attttcaggt    3360
tttgaaagac attaacctcg gaagttgttt ttaagaatta ttctcataat tcttattctc    3420
ataatttctg taatccacct caagcttcat agttatttgg cattgaaata acacccagag    3480
catgatagaa atgttgttac tcttcctctc tcaaggagaa agtaattttc ctgcaatact    3540
taataattgg caccgttgct ttctaaagac tccatggtgc attcaagagt atccaacttc    3600
aagggaatct ccgcatttca atgaaaggag gaagagtgtg ctgataaacc taccagcacc    3660
tattgagcaa tgtctattat agtaattttg catacatttt tatttaaggg aaaaaatata    3720
ggtattgtga atattttgc taatcttata gaaaaggaaa aaatcccgtt atttaaaggg    3780
aaaagtaaat ttaacagttg cctttttct taatgtcagg gcagatctta ttttacagta    3840
cagtggggga aatagaaaca tgtgaaaggc aaaaggcagg ctcctaaatt aatgtcagtg    3900
aagttcaggg tgggcaaatg agtgtgtgtg aggtatagga aatgctgatg acttctttaa    3960
tgcttgaagt ccgttcacag gtatctagcc ctagaatgcc tagaacagga agaggcagct    4020
ggtgttctgc aaaacttgga caggggcaaa gttgctgaaa aagttttggt ttaacccgaa    4080
gataagtgga aaagagcttg tccatgaacc caggttctca ctctgtttac agaagtgtgt    4140
tgagtacagt tggtgaagga agaggtaaca aaaaatgcta aatattttat ccatgaaaat    4200
gacttccaga aaaggaagaa tatgaacccc agaccgaagg ggaaaagata gttaatagta    4260
ttatctaacc tggttggtat ttgtaatgaa tggtgatttt aattagtcat tagccataat    4320
gatgtttatt tacagtataa ctcctgaatg ctacttaaat aaaccaggat tcaaactgca    4380
agccagccag gccgttcatt atttaaaacg ttttaatcgg ggcttccggg tagaaggtgg    4440
agcggcaggg tgtaattggg ttgatgggtg ggacctgtct tgaccatcgg agttttataa    4500
tcgagggcca ggagggcccg ggttgctctc ctggttatgt atgtacttgt acataaccac    4560
ctaaagaatg gtgaaataaa tgttcttgga aattccta                            4598
```

<210> SEQ ID NO 5
<211> LENGTH: 21
<212> TYPE: RNA
<213> ORGANISM: Artificial Sequence
<220> FEATURE:
<223> OTHER INFORMATION: small interfering RNA
<220> FEATURE:
<221> NAME/KEY: misc_feature
<222> LOCATION: 1, 2
<223> OTHER INFORMATION: n = A,G, U or C

<400> SEQUENCE: 5

```
nncaugaagc agcacgacuu c                                                21
```